(12) United States Patent
Fogarty et al.

(10) Patent No.: US 10,959,825 B2
(45) Date of Patent: Mar. 30, 2021

(54) INTRAVASCULAR IMPLANTS AND METHODS OF USING THE SAME

(71) Applicant: Thomas J. Fogarty, Mountain View, CA (US)

(72) Inventors: Thomas J. Fogarty, Portola Valley, CA (US); Michael J. Drews, Palo Alto, CA (US); Neil D. Holmgren, Chicago, IL (US); D. Bruce Modesitt, San Carlos, CA (US)

(73) Assignee: Thomas J. Fogarty, Los Altos, CA (US)

( * ) Notice: Subject to any disclaimer, the term of this patent is extended or adjusted under 35 U.S.C. 154(b) by 0 days.

(21) Appl. No.: 15/670,797

(22) Filed: Aug. 7, 2017

(65) Prior Publication Data

US 2017/0360553 A1     Dec. 21, 2017

Related U.S. Application Data

(63) Continuation of application No. 15/284,381, filed on Oct. 3, 2016, now Pat. No. 9,744,026, which is a
(Continued)

(51) Int. Cl.
*A61F 2/07* (2013.01)
*A61F 2/88* (2006.01)
(Continued)

(52) U.S. Cl.
CPC ................. *A61F 2/07* (2013.01); *A61F 2/88* (2013.01); *A61F 2/89* (2013.01);
(Continued)

(58) Field of Classification Search
CPC ...... A61F 2/07; A61F 2/013; A61F 2002/016; A61F 2220/0008; A61F 2/06;
(Continued)

(56) References Cited

U.S. PATENT DOCUMENTS 2,903,365 A    9/1959  O'Brian et al.
3,834,394 A    9/1974  Hunter et al.
(Continued)

FOREIGN PATENT DOCUMENTS

AU    2003/204493    12/2003
FR       2689388    10/1993
(Continued)

OTHER PUBLICATIONS

FR 2689388—English Abstract.
(Continued)

*Primary Examiner* — Brian E Pellegrino
(74) *Attorney, Agent, or Firm* — Levine Bagade Han LLP

(57) ABSTRACT

An intravascular implant and methods of using the implant within the vasculature of the body, for example near a vascular aneurysm, are disclosed. A method of treating an aneurysm includes positioning a vascular graft comprising a tubular channel having a first end and a second end in a blood vessel, securing the vascular graft in place with an expandable anchoring member, and filling a seal cuff on the vascular graft, wherein the seal cuff extends radially outward beyond an exterior surface of the vascular graft, wherein the seal cuff comprises a first seal portion and a second seal portion and wherein the first seal portion is separated from the second seal portion by a first gap and a second gap along a circumference of the seal cuff.

17 Claims, 27 Drawing Sheets

Related U.S. Application Data continuation of application No. 13/666,756, filed on Nov. 1, 2012, now Pat. No. 9,615,912, which is a continuation of application No. 11/351,423, filed on Feb. 10, 2006, now abandoned, which is a continuation of application No. 10/778,870, filed on Feb. 12, 2004, now abandoned.

(60) Provisional application No. 60/447,056, filed on Feb. 12, 2003.

(51) Int. Cl.
  *A61F 2/06* (2013.01)
  *A61F 2/89* (2013.01)

(52) U.S. Cl.
  CPC ... *A61F 2002/065* (2013.01); *A61F 2002/068* (2013.01); *A61F 2002/075* (2013.01); *A61F 2220/0075* (2013.01); *A61F 2250/0069* (2013.01)

(58) Field of Classification Search
  CPC ........ A61F 2220/0075; A61F 2002/823; A61F 2/856; A61F 2002/068; A61F 2250/0069
  See application file for complete search history.

(56) References Cited

U.S. PATENT DOCUMENTS

| | | |
|---|---|---|
| 4,085,757 A | 4/1978 | Pevsner |
| 4,108,173 A | 8/1978 | Silvenko |
| 4,301,803 A | 11/1981 | Handa et al. |
| 4,341,218 A | 7/1982 | U |
| 4,346,712 A | 8/1982 | Handa et al. |
| 4,553,545 A | 11/1985 | Maass et al. |
| 4,577,631 A | 3/1986 | Kreamer |
| 4,638,803 A | 1/1987 | Rand |
| 4,641,653 A | 2/1987 | Rockey |
| 4,728,328 A | 3/1988 | Hughes et al. |
| 4,944,745 A | 7/1990 | Sogard et al. |
| 4,994,069 A | 2/1991 | Ritchart et al. |
| 5,078,726 A | 1/1992 | Kreamer |
| 5,104,404 A | 4/1992 | Wolff |
| 5,133,731 A | 7/1992 | Butler et al. |
| 5,151,105 A | 9/1992 | Kwan-Gett |
| 5,156,620 A | 10/1992 | Pigott |
| 5,163,953 A | 11/1992 | Vince |
| 5,181,921 A | 1/1993 | Makita et al. |
| 5,192,301 A | 3/1993 | Kamiya et al. |
| 5,226,911 A | 7/1993 | Chee et al. |
| 5,282,824 A | 2/1994 | Gianturco |
| 5,308,356 A | 5/1994 | Blackshear, Jr. et al. |
| 5,312,415 A | 5/1994 | Palermo |
| 5,330,528 A | 7/1994 | Lazim |
| 5,334,217 A | 8/1994 | Das |
| 5,360,443 A | 11/1994 | Barone et al. |
| 5,395,333 A | 3/1995 | Brill |
| 5,411,550 A | 5/1995 | Herweck et al. |
| 5,478,309 A | 12/1995 | Sweezer et al. |
| 5,534,024 A | 7/1996 | Rogers et al. |
| 5,540,711 A | 7/1996 | Kieturakis et al. |
| 5,558,642 A | 9/1996 | Schweich, Jr. et al. |
| 5,575,817 A | 11/1996 | Martin |
| 5,578,071 A | 11/1996 | Parodi |
| 5,582,619 A | 12/1996 | Ken |
| 5,591,195 A | 1/1997 | Taheri et al. |
| 5,593,442 A | 1/1997 | Klein |
| 5,613,981 A | 3/1997 | Boyle et al. |
| 5,628,783 A | 5/1997 | Quiachon et al. |
| 5,665,117 A | 9/1997 | Rhodes |
| 5,667,767 A | 9/1997 | Greff et al. |
| 5,693,088 A | 12/1997 | Lazarus |
| 5,702,361 A | 12/1997 | Evans et al. |
| 5,704,910 A * | 1/1998 | Humes ............... A61F 2/01 604/502 |
| 5,713,917 A | 2/1998 | Leonhardt et al. |
| 5,725,568 A | 3/1998 | Hastings |
| 5,728,131 A | 3/1998 | Frantzen et al. |
| 5,749,894 A | 5/1998 | Engelson |
| 5,752,974 A | 5/1998 | Rhee et al. |
| 5,766,160 A | 6/1998 | Samson et al. |
| 5,769,882 A | 6/1998 | Fogarty et al. |
| 5,779,672 A | 7/1998 | Dormandy |
| 5,785,679 A | 7/1998 | Abolfathi et al. |
| 5,795,331 A | 8/1998 | Cragg et al. |
| 5,800,526 A | 9/1998 | Anderson et al. |
| 5,823,198 A | 10/1998 | Jones et al. |
| 5,824,037 A | 10/1998 | Fogarty et al. |
| 5,824,040 A | 10/1998 | Cox et al. |
| 5,830,230 A | 11/1998 | Berryman et al. |
| 5,843,160 A | 12/1998 | Rhodes |
| 5,861,003 A | 1/1999 | Latson et al. |
| 5,876,448 A | 3/1999 | Thompson et al. |
| 5,916,235 A | 6/1999 | Guglielmi |
| 5,925,059 A | 7/1999 | Palermo et al. |
| 5,928,260 A | 7/1999 | Chin et al. |
| 5,935,145 A | 8/1999 | Villar et al. |
| 5,944,733 A | 8/1999 | Engelson |
| 5,951,599 A | 9/1999 | McCrory |
| 5,980,514 A | 11/1999 | Kupiecki et al. |
| 5,984,963 A | 11/1999 | Ryan et al. |
| 6,015,424 A | 1/2000 | Rosenbluth et al. |
| 6,015,431 A | 1/2000 | Thornton et al. |
| 6,024,754 A | 2/2000 | Engelson |
| 6,059,823 A | 5/2000 | Holman et al. |
| 6,063,121 A | 5/2000 | Xavier et al. |
| 6,066,149 A | 5/2000 | Samson et al. |
| 6,080,194 A | 6/2000 | Pachence et al. |
| 6,093,199 A | 7/2000 | Brown et al. |
| 6,096,021 A | 8/2000 | Helm et al. |
| 6,102,940 A | 8/2000 | Robichon et al. |
| 6,110,198 A | 8/2000 | Fogarty et al. |
| 6,113,629 A | 9/2000 | Ken |
| 6,136,015 A | 10/2000 | Kurz et al. |
| 6,139,520 A | 10/2000 | McCrory et al. |
| 6,146,373 A | 11/2000 | Cragg et al. |
| 6,149,664 A | 11/2000 | Kurz |
| 6,152,956 A | 11/2000 | Pierce |
| 6,165,193 A | 12/2000 | Greene, Jr. et al. |
| 6,165,194 A | 12/2000 | Denardo |
| 6,168,592 B1 | 1/2001 | Kupiecki et al. |
| 6,190,402 B1 | 2/2001 | Horton et al. |
| 6,193,745 B1 | 2/2001 | Fogarty et al. |
| 6,196,230 B1 | 3/2001 | Hall et al. |
| 6,203,550 B1 | 3/2001 | Olson |
| 6,203,779 B1 | 3/2001 | Ricci et al. |
| 6,214,036 B1 | 4/2001 | Letendre et al. |
| 6,231,562 B1 | 5/2001 | Khosravi et al. |
| 6,238,403 B1 | 5/2001 | Greene, Jr. et al. |
| 6,248,122 B1 | 6/2001 | Klumb et al. |
| 6,261,305 B1 | 7/2001 | Marotta et al. |
| 6,273,909 B1 | 8/2001 | Kugler et al. |
| 6,273,917 B1 | 8/2001 | Inoue |
| 6,283,991 B1 | 9/2001 | Cox et al. |
| 6,287,315 B1 | 9/2001 | Wijeratne et al. |
| 6,287,335 B1 | 9/2001 | Drasler et al. |
| 6,290,731 B1 | 9/2001 | Solovay et al. |
| 6,293,960 B1 | 9/2001 | Ken |
| 6,296,603 B1 | 10/2001 | Turnlund et al. |
| 6,296,604 B1 | 10/2001 | Garibaldi et al. |
| 6,299,597 B1 | 10/2001 | Buscemi et al. |
| 6,299,619 B1 | 10/2001 | Greene, Jr. et al. |
| 6,312,421 B1 | 11/2001 | Boock |
| 6,312,462 B1 | 11/2001 | McDermott et al. |
| 6,312,463 B1 | 11/2001 | Rourke et al. |
| 6,315,709 B1 | 11/2001 | Garibaldi et al. |
| 6,319,276 B1 | 11/2001 | Holman et al. |
| 6,325,819 B1 | 12/2001 | Pavcnik et al. |
| 6,331,184 B1 | 12/2001 | Abrams |
| 6,334,869 B1 | 1/2002 | Leonhardt et al. |
| 6,344,041 B1 | 2/2002 | Kupiecki et al. |
| 6,344,048 B1 | 2/2002 | Chin et al. |
| 6,344,056 B1 | 2/2002 | Dehdashtian |
| 6,350,270 B1 | 2/2002 | Roue |

(56) References Cited

U.S. PATENT DOCUMENTS

| | | |
|---|---|---|
| 6,358,556 B1 | 3/2002 | Ding et al. |
| 6,361,556 B1 | 3/2002 | Chuter |
| 6,364,823 B1 | 4/2002 | Garibaldi et al. |
| 6,375,668 B1 | 4/2002 | Gifford et al. |
| 6,375,669 B1 | 4/2002 | Rosenbluth et al. |
| 6,379,329 B1 | 4/2002 | Naglreiter et al. |
| 6,383,174 B1 | 5/2002 | Eder |
| 6,395,019 B2 | 5/2002 | Chobotov |
| 6,409,757 B1 | 6/2002 | Trout, III et al. |
| 6,458,119 B1 | 10/2002 | Berenstein et al. |
| 6,463,317 B1 | 10/2002 | Kucharczyk et al. |
| 6,486,510 B2 | 11/2002 | Camrud et al. |
| 6,494,889 B1 | 12/2002 | Fleischman et al. |
| 6,506,204 B2 | 1/2003 | Mazzocchi |
| 6,511,468 B1 | 1/2003 | Cragg et al. |
| 6,521,244 B1 | 2/2003 | Kanesaka |
| 6,527,739 B1 | 3/2003 | Bigus et al. |
| 6,544,219 B2 | 4/2003 | Happ et al. |
| 6,544,276 B1 | 4/2003 | Azizi |
| 6,551,280 B1 | 4/2003 | Knighton et al. |
| 6,551,303 B1 | 4/2003 | Van Tassel et al. |
| 6,558,367 B1 | 5/2003 | Cragg et al. |
| 6,565,602 B2 | 5/2003 | Rolando et al. |
| 6,585,756 B1 | 7/2003 | Strecker |
| 6,585,760 B1 | 7/2003 | Fogarty |
| 6,589,265 B1 | 7/2003 | Palmer et al. |
| 6,592,614 B2 | 7/2003 | Lenker et al. |
| 6,613,037 B2 | 9/2003 | Khosravi et al. |
| 6,613,074 B1 | 9/2003 | Mitelberg et al. |
| 6,616,684 B1 | 9/2003 | Vidlund et al. |
| 6,626,928 B1 | 9/2003 | Raymond et al. |
| 6,626,938 B1 | 9/2003 | Butaric et al. |
| 6,629,947 B1 | 10/2003 | Sahatjian et al. |
| 6,645,167 B1 | 11/2003 | Whalen, II et al. |
| 6,656,214 B1 | 12/2003 | Fogarty et al. |
| 6,663,607 B2 | 12/2003 | Saikeu et al. |
| 6,663,667 B2 | 12/2003 | Dehdashtian et al. |
| 6,692,510 B2 | 2/2004 | West |
| 6,695,876 B1 | 2/2004 | Marotta et al. |
| 6,712,826 B2 | 3/2004 | Lui |
| 6,723,108 B1 | 4/2004 | Jones et al. |
| 6,729,356 B1 | 5/2004 | Baker et al. |
| 6,730,119 B1 | 5/2004 | Smalling |
| 6,764,510 B2 | 7/2004 | Vidlund et al. |
| 6,827,735 B2 | 12/2004 | Greenberg |
| 6,843,803 B2 | 1/2005 | Ryan et al. |
| 6,852,097 B1 | 2/2005 | Fulton, III |
| 6,921,410 B2 | 7/2005 | Porter |
| 7,011,676 B2 | 3/2006 | Dong |
| 7,070,609 B2 | 7/2006 | West |
| 7,070,616 B2 | 7/2006 | Majercak et al. |
| 7,081,129 B2 | 7/2006 | Chobotov |
| 7,101,396 B2 | 9/2006 | Artof et al. |
| 7,128,736 B1 | 10/2006 | Abrams et al. |
| 7,147,660 B2 | 12/2006 | Chobotov et al. |
| 7,147,661 B2 | 12/2006 | Chobotov et al. |
| 7,530,988 B2 | 5/2009 | Evans et al. |
| 7,615,071 B2 | 11/2009 | Chobotov |
| 7,708,771 B2 | 5/2010 | Chuter et al. |
| 8,231,665 B2 | 7/2012 | Kim et al. |
| 8,231,666 B2 | 7/2012 | Kim et al. |
| 8,262,686 B2 | 9/2012 | Fogarty et al. |
| 8,361,136 B2 | 1/2013 | Chobotov |
| 8,535,367 B2 | 9/2013 | Kim et al. |
| 8,562,662 B2 | 10/2013 | Kim et al. |
| 8,647,377 B2 | 2/2014 | Kim et al. |
| 8,801,769 B2 | 8/2014 | Chobotov |
| 8,936,633 B2 | 1/2015 | Kim et al. |
| 9,295,569 B2 | 3/2016 | Kim et al. |
| 9,561,037 B2 | 2/2017 | Fogarty et al. |
| 9,561,096 B2 | 2/2017 | Kim et al. |
| 9,561,097 B1 | 2/2017 | Kim et al. |
| 9,615,912 B2 | 4/2017 | Fogarty et al. |
| 9,629,636 B2 | 4/2017 | Fogarty et al. |
| 9,750,504 B2 | 9/2017 | Fogarty et al. |
| 9,913,651 B2 | 3/2018 | Fogarty et al. |
| 10,383,636 B2 | 8/2019 | Fogarty et al. |
| 10,470,868 B2 | 11/2019 | Kim et al. |
| 10,470,869 B2 | 11/2019 | Kim et al. |
| 2001/0020184 A1 | 9/2001 | Dehdashtian et al. |
| 2001/0044621 A1 | 11/2001 | Klumb et al. |
| 2001/0047202 A1 | 11/2001 | Slaikeu et al. |
| 2002/0019665 A1 | 2/2002 | Dehdashtian et al. |
| 2002/0026217 A1 | 2/2002 | Baker et al. |
| 2002/0045848 A1 | 4/2002 | Jaafar et al. |
| 2002/0052643 A1 | 5/2002 | Wholey et al. |
| 2002/0058986 A1 | 5/2002 | Landau et al. |
| 2002/0065542 A1 | 5/2002 | Lax et al. |
| 2002/0077693 A1 | 6/2002 | Barclay et al. |
| 2002/0082638 A1 | 6/2002 | Porter et al. |
| 2002/0082682 A1 | 6/2002 | Barclay et al. |
| 2002/0099441 A1 | 7/2002 | Dehdashtian |
| 2002/0107565 A1 | 8/2002 | Greenhalgh |
| 2002/0151957 A1 | 10/2002 | Kerr |
| 2002/0169497 A1 | 11/2002 | Wholey et al. |
| 2002/0183841 A1 | 12/2002 | Cohn et al. |
| 2002/0193821 A1 | 12/2002 | Trout |
| 2003/0004531 A1 | 1/2003 | Jones et al. |
| 2003/0014075 A1 | 1/2003 | Rosenbluth et al. |
| 2003/0028209 A1 | 2/2003 | Teoh et al. |
| 2003/0051735 A1 | 3/2003 | Pavcnik et al. |
| 2003/0074017 A1 | 4/2003 | Shah |
| 2003/0130724 A1 | 7/2003 | DePalma et al. |
| 2003/0171805 A1 | 9/2003 | Berg et al. |
| 2003/0195607 A1 | 10/2003 | Trout et al. |
| 2003/0204246 A1 | 10/2003 | Chu et al. |
| 2003/0216802 A1 | 11/2003 | Chobotov |
| 2003/0220666 A1 | 11/2003 | Mirigian et al. |
| 2003/0220667 A1 | 11/2003 | van der Burg et al. |
| 2003/0229286 A1 | 12/2003 | Lenker |
| 2004/0044358 A1 | 3/2004 | Khosravi et al. |
| 2004/0044361 A1 | 3/2004 | Frazier et al. |
| 2004/0073190 A1 | 4/2004 | Deem et al. |
| 2004/0073288 A1 | 4/2004 | Kerr |
| 2004/0098027 A1 | 5/2004 | Teoh et al. |
| 2004/0116997 A1 | 6/2004 | Taylor et al. |
| 2004/0186556 A1 | 9/2004 | Hogendijk et al. |
| 2004/0210249 A1 | 10/2004 | Fogarty et al. |
| 2004/0254625 A1 | 12/2004 | Stephens et al. |
| 2005/0249776 A1 | 11/2005 | Chen et al. |
| 2006/0292206 A1 | 12/2006 | Kim et al. |
| 2007/0050008 A1 | 3/2007 | Kim et al. |
| 2007/0055355 A1 | 3/2007 | Kim et al. |
| 2007/0061005 A1 | 3/2007 | Kim et al. |
| 2008/0275536 A1 | 11/2008 | Zarins et al. |
| 2012/0179192 A1 | 7/2012 | Fogarty et al. |
| 2012/0265287 A1 | 10/2012 | Sharma et al. |
| 2012/0330343 A1 | 12/2012 | Kim et al. |
| 2013/0060320 A1 | 3/2013 | Fogarty et al. |
| 2014/0081374 A1 | 3/2014 | Kim et al. |
| 2014/0088690 A1 | 3/2014 | Fogarty et al. |
| 2014/0142685 A1 | 5/2014 | Kim et al. |
| 2017/0020653 A1 | 1/2017 | Kim et al. |
| 2017/0020654 A1 | 1/2017 | Fogarty et al. |
| 2017/0086853 A1 | 3/2017 | Fogarty et al. |
| 2017/0333047 A1 | 11/2017 | Fogarty et al. |
| 2018/0199946 A1 | 7/2018 | Fogarty et al. |
| 2019/0321051 A1 | 10/2019 | Fogarty et al. |
| 2020/0022801 A1 | 1/2020 | Kim et al. |
| 2020/0022802 A1 | 1/2020 | Kim et al. |

FOREIGN PATENT DOCUMENTS

| | | |
|---|---|---|
| WO | WO 1999/016384 | 4/1999 |
| WO | WO 1999/043273 | 9/1999 |
| WO | WO 1999/065418 | 12/1999 |
| WO | WO 2000/069367 | 11/2000 |
| WO | WO 2001/006950 | 2/2001 |
| WO | WO 2001/028434 | 4/2001 |
| WO | WO 2001/093920 | 12/2001 |

(56) References Cited

FOREIGN PATENT DOCUMENTS

WO     WO 2002/02282     12/2002
WO     WO 2004/045393     6/2004

OTHER PUBLICATIONS

Franklin et al, "Uptake of Tetracycline by Aortic Aneurysm Wall and Its Effect on Inflammation and Proteolysis," *Brit. J. Surgery*, 86(6):771-775, 1999.

Pyo et al, "Targeted Gene Disruption of Matrix Metalloproteinase-9 (Gelatinase B) Suppresses Development of Experimental Abdominal Aortic Aneurysms," *J. Clinical Investigation*, 105(11):1641-1649, 2000.

Tambiah et al, "Provocation of Experimental Aortic Inflammation Mediators and Chlamydia Pneumoniae," *Brit. J. Surgery*: 88(7):935-940, 2001.

Villareal et al, "Early Results Using Bare Metal Stents With or Without Coil Embolization for AAA Exclusion," *Journal of endovascular therapy : an official journal of the International Society of Endovascular Specialists*, 8 pages, 2001.

Walton, et al, "Inhibition of Prostogiandin E2 Synthesis in Abdominal Aortic Aneurysms," *Circulation*, pp. 48-54, Jul. 6, 1999.

Xu et al, "Sp 1 increases Expression of Cyclooxygenase-2 in Hypoxic Vascuar Endothelium," *J. Biological Chemistry*, 275(32):24583-24589, 2000.

\* cited by examiner

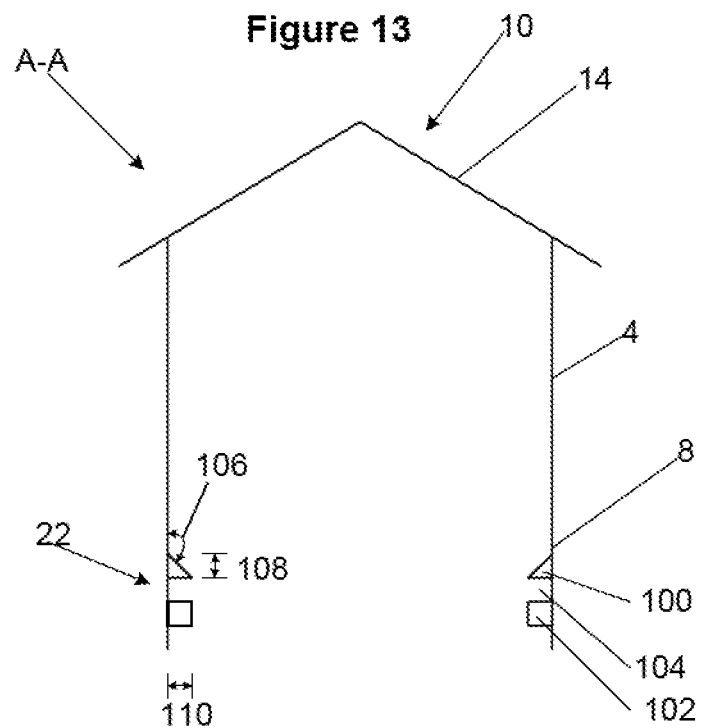
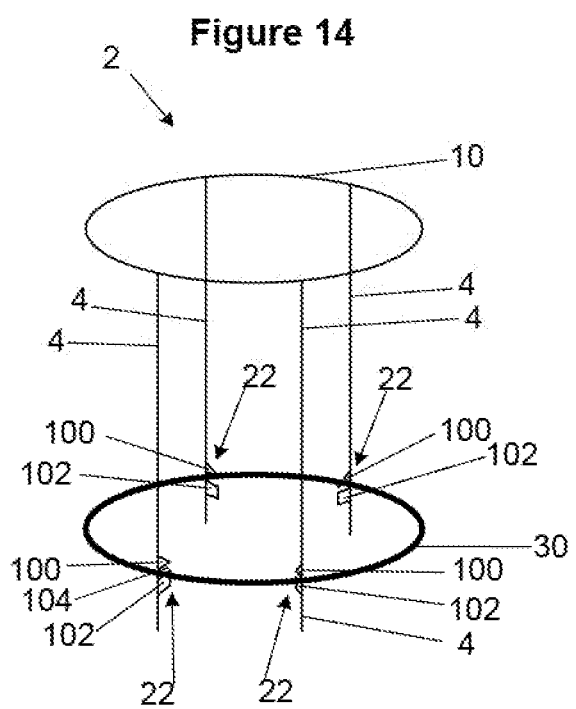

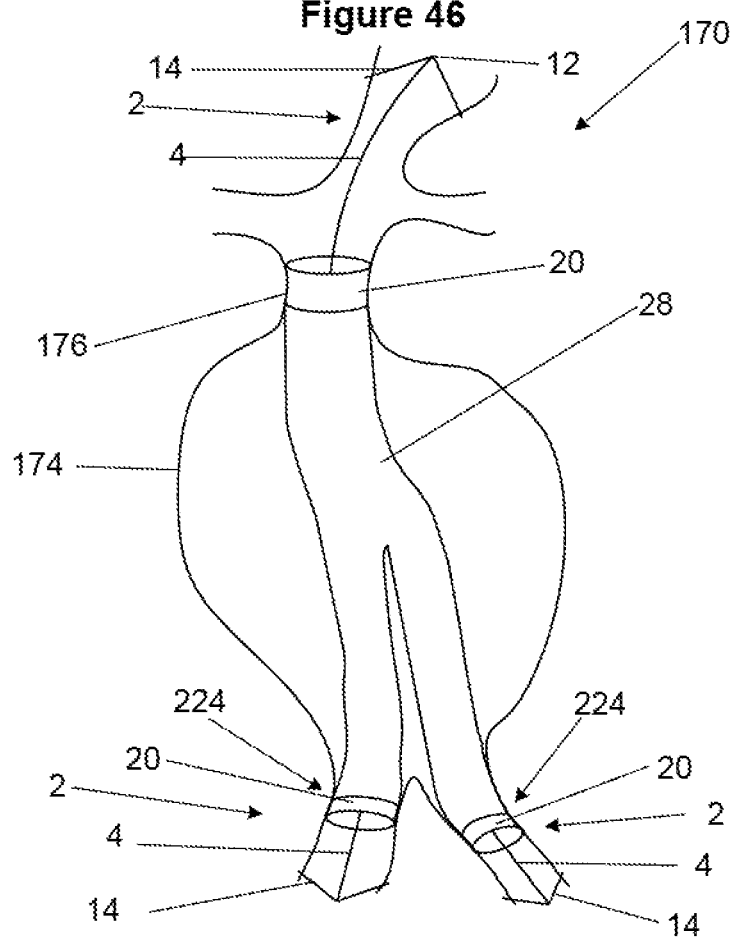

INTRAVASCULAR IMPLANTS AND METHODS OF USING THE SAME

CROSS-REFERENCE TO RELATED APPLICATIONS

This application is a continuation of U.S. patent application Ser. No. 15/284,381 filed Oct. 3, 2016, which is a continuation of U.S. patent application Ser. No. 13/666,756 filed Nov. 1, 2012 (now U.S. Pat. No. 9,615,912), which is a continuation of U.S. patent application Ser. No. 11/351,423 filed Feb. 10, 2006 (now abandoned), which is a continuation of U.S. patent application Ser. No. 10/778,870 filed Feb. 12, 2004 (now abandoned), which claims the benefit of U.S. Provisional Application No. 60/447,056 filed Feb. 12, 2003, the contents of all which are incorporated herein by reference in their entireties.

BACKGROUND OF THE INVENTION

1. Field of the Invention

The present invention relates generally to an intravascular implant and methods of using the implant within the vasculature of the body, particularly adjacent to vascular aneurysms. The present invention also relates to the attachment of a second implant, such as a vascular graft, to the intravascular implant.

2. Description of the Related Art

An aneurysm is an abnormal dilatation of a biological vessel. Aneurysms can alter flow through the affected vessel and often decrease the strength of the vessel wall, thereby increasing the vessel's risk of rupturing at the point of dilation or weakening. Implanting a vascular prosthesis through the vessel with the aneurysm is a common aneurysm therapy. Vascular grafts and stent grafts (e.g., ANEURX® Stent Graft System from Medtronic AVE, Inc., Santa Rosa, Calif.) are examples of vascular prostheses used to treat aneurysms by reconstructing the damaged vessel.

Stent grafts rely on a secure attachment to the proximal, or upstream, neck of an aneurysm, particularly for aortic abdominal aneurysms (AAA), but several factors can interfere with this attachment. The proximal neck of the aneurysm can be diseased. This diseased tissue can by a calcified and/or irregularly shaped tissue surface for which the graft must to attach. Healthy, easily-attachable tissue is often a distance away from the aneurysm. For example, in AAAs the nearest healthy vascular tissue may be above the renal arteries. Even a healthy vessel can be so irregularly shaped or tortuous that a graft may have difficulty attaching and staying sealed. Furthermore, the proximal neck can shift locations and geometries over time, particularly over the course of aneurysm treatment and reformation of the aneurysmal sack. This shifting and shape changing of the vessel can result in partial or total dislodgement of the proximal end of a currently available stent graft.

Devices have been developed that attempt to solve the issue of vascular graft attachment. International Publication No. WO 00/69367 by Strecker discloses an aneurysm stent. The stent has a securing mechanism that attaches to the vascular wall proximal to the renal arteries, which is typically where healthier vascular tissue is located when a patient has an AAA. The stent also has a membrane that is placed at the proximal end of a stent graft and forms a seal in the vessel. Strecker, however, discloses a securing mechanism with ball-ended struts which angle away from the seal. The ball-ends will reduce the pressure applied by the struts onto the vascular wall, and the struts are angled improperly to insure the best anchor. If the graft begins to dislodge into the aneurysm, the struts will tend to fold inward and slide with the graft instead of engaging frictionally into the vascular walls to prevent dislodgement.

U.S. Pat. No. 6,152,956 to Pierce discloses a radially expandable collar connected by connecting wires to an expandable stent. The stent also has barbs with sharp ends that spring radially outward to embed into the walls of the vascular tissue. The stent, however, is expandable, but once expanded cannot be easily contracted. The stent, therefore, can not be repositioned if incorrectly placed during initial deployment. Further, the barbs do not angle toward the seal and will not engage into the vascular wall for additional anchoring force, should the prosthesis begin to become dislodged.

U.S. Pat. No. 6,361,556 by Chuter discloses a stent for attaching to grafts, where the stent is connected to an attachment system for anchoring to the vessel. The attaching system has hooks angled toward the graft. The attachment system has no way of being repositioned during deployment. Further, the stent is a substantially rigid, balloon expandable stent and therefore maintains a fixed diameter and resists deformation from forces imposed by the vascular environment. The stent, therefore, can not be easily repositioned during deployment and may not seal the graft under changing geometric conditions over time.

There is thus a need for a device and method that can securely anchor a vascular graft within a vessel and can seal the graft regardless of the existence of diseased tissue at the sealing location. There is also a need for a device that can be deployed to the vasculature while minimizing bloodflow obstruction to the main vessel and to branching vessels. A need also exists for a device and method that can accomplish the above needs and adjust to tortuous vasculature. There is also a need for a device and method that can accomplish the above and have dimensions and a placement location that can be adjusted multiple times in vivo, even after the anchor has been fully deployed. There is also a need for a device that can be delivered through a low profile catheter. Additionally, there is a need for a device that can anchor into a different portion of tissue from which it seals, so as not to overstress any individual portion of vascular tissue or any elements of the implant, thus preventing fractures in the tissue and of the implant.

BRIEF SUMMARY OF THE INVENTION

One embodiment of the disclosed intravascular implant has a seal, a connector, and an anchor. The seal is configured to attach to a second implant. The connector has a first end and a second end. The first end is attached to the seal, and the second end is attached to the anchor. The anchor has an arm, and the arm is angled toward the seal as the arm extends radially away from the center of the anchor. The anchor can be formed of multiple radially extending tines or arms such as an uncovered umbrella structure, a hook and/or a barb.

Another embodiment of the disclosed intravascular implant has a seal and a substantially cylindrical coil, where the coil is attached to, and extends from, the seal. The seal can also have a gasket. The seal can also have an inflatable collar.

Yet another embodiment of the intravascular implant has a seal, a connector and an anchor. The seal is configured to attach to a second implant. The connector has a first end and a second end and may be flexible. The first end is attached to the seal, and the second end is attached to the anchor. The connector may be formed of a coil. The connector can be configured to allow for longitudinal adjustments. The distance between the seal and the anchor can be changed. The implant can also have a second anchor to assist in additional fixation.

Another embodiment of the intravascular implant has a seal, a connector, an anchor, and a stop. The connector has a first end and a second end. The first end is attached to the seal, and the second end is attached to the anchor. The anchor has an arm and the arm is angled toward the seal as the arm extends radially from the center of the anchor. Radial extension of the arm is limited by the stop. The stop can be a mechanical interference.

Yet another embodiment of the disclosed intravascular implant has a seal, a connector and an anchor. The connector has a flexible member, a first end and a second end. The first end is attached to the seal and the second end is attached to the anchor. The anchor has an arm. The arm angles toward the seal as the arm extends radially from the center of the anchor. The seal can have a gasket. The seal can have an inflatable collar. The connector can have a coil. The implant can also have a second anchor.

BRIEF DESCRIPTION OF THE DRAWINGS

FIG. 13 illustrates an embodiment of cross-section A-A of the intravascular implant without the seal.

FIG. 14 is a front perspective view of an embodiment of the intravascular implant.

FIG. 46 illustrates an embodiment of the intravascular implant after deployment into a vascular site.

DETAILED DESCRIPTION

Figure 1:
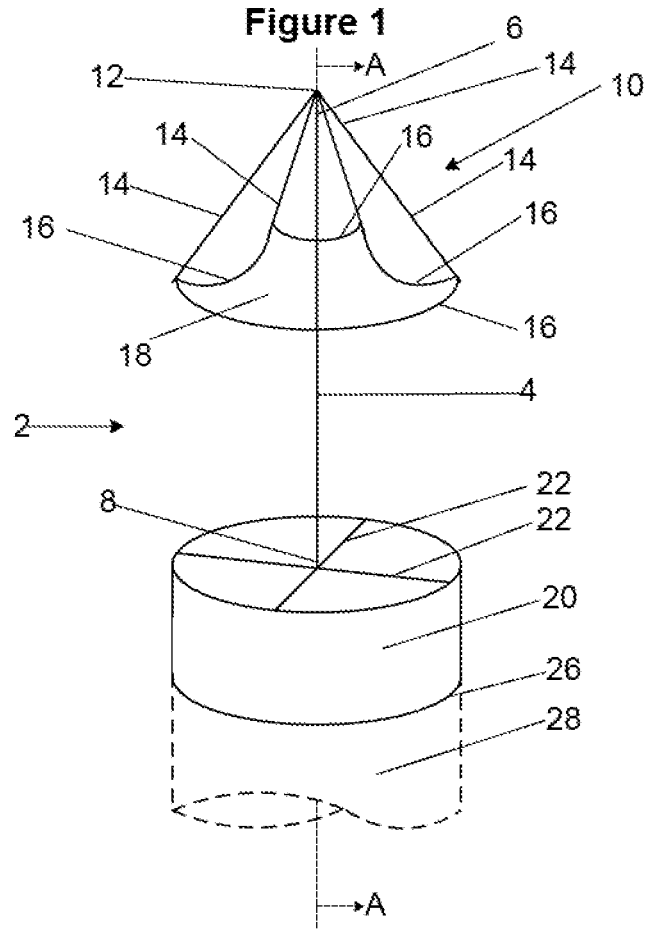
FIG. 1 is a front perspective view of an embodiment of the intravascular implant.

FIG. 1 illustrates an embodiment of an intravascular implant 2. The implant 2 can have a connector 4 having a first end 6 and a second end 8. The first end 6 can be attached to an anchor 10. The anchor 10 can have a central tip 12. The central tip 12 can be attached to the first end 6. The anchor 10 can also have multiple tines or arms 14 extending radially from the central tip 12, such as in an uncovered umbrella structure. The central tip 12 can be rotatably or flexibly attached to the arms 14. Leaves 16 can be attached at two ends to adjacent arms 14. A flow-through area 18 can be an open port defined by any leaf 16 and the arms 14 to which that leaf 16 attaches.

The second end 8 can be attached to a seal 20. The second end 8 can attach to the seal 20 through an attachment device 22, for example struts. The attachment device 22 can be integral with the second end 8, integral with the seal 20, or an independent part. Attachment devices 22 can also be used to attach the connector 4 to the anchor 10. The seal 20 can have a first proximal end 24 and a first distal end 26. A second implant 28 can be attached to the seal 20, for example at the distal end 26, or the second implant 28 can be an integral part of the seal 20.

Figure 2:
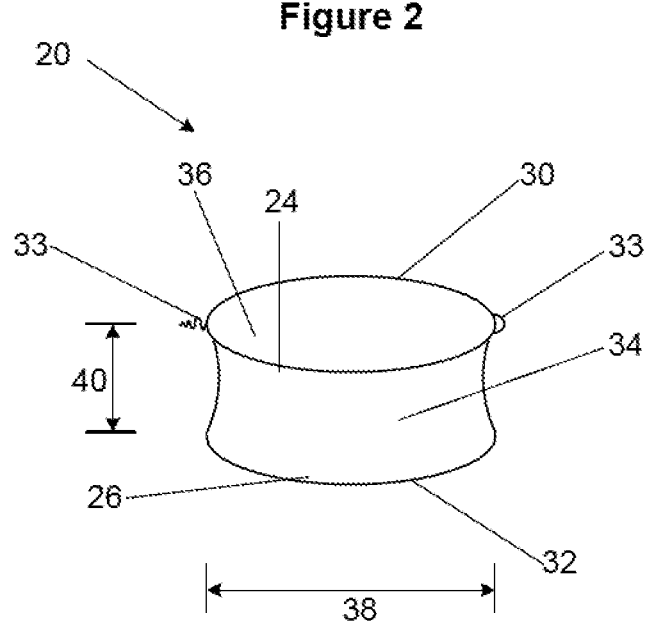
FIGS. 2 and 3 are front perspective views of various embodiments of the seal.

FIG. 2 illustrates a single gasket embodiment of the seal 20. The seal 20 can have a first seal ring 30 at the proximal end 24. The seal 20 can also have a second seal ring 32 at the distal end 26. The seal rings 30 and 32 can have radially extending spring force elements or tissue mainstays 33. The tissue mainstays 33 can be, for example a barb, spike, hook, peg, a coil, pigtail or leaf spring, or any combination thereof. The seal rings 30 and 32 can be made from nickel-titanium alloy (e.g., Nitinol), titanium, stainless steel, cobalt-chrome alloy (e.g., ELGILOY® from Elgin Specialty Metals, Elgin, Ill.; CONICHROME® from Carpenter Metals Corp., Wyomissing, Pa.), polymers such as polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, silicone, radiopaque materials, or any combination thereof. Examples of radiopaque materials are barium, sulfate, titanium, stainless steel, nickel-titanium alloys and gold.

The seal 20 can have a first seal cover 34 attached at the proximal end 24 to the first seal ring 30 and at the distal end 26 to the second seal ring 32. The seal cover 34 can be made from polymers such as polyester (e.g., DACRON® from E. I. Du Pont de Nemours and Company, Wilmington, Del.), polypropylene, PTFE, ePTFE, PEEK, nylon, polylactic acid (PLA), poly(lactic-co-glycolic acid) (PLGA), polyglycolic acid (PGA), polyurethane, polyethylene, vascular, valvular or pericardial tissue, extruded collagen, silicone, metal mesh, radiopaque materials, or any combination thereof.

A seal flow port 36 can be the hole defined by the inner radii of the seal rings 30 and 32 and the seal cover 34. The seal 20 can have a seal diameter 38 that can depend on the diameter of the vessel in a given patient. The seal diameter 38 can be from about 5 mm (0.2 in.) to about 50 mm (2.0 in.), for example about 30 mm (1.2 in.). The seal 20 can have a seal height 40 from about 1 mm (0.04 in.) to about 6 cm (2.4 in.).

Figure 3:
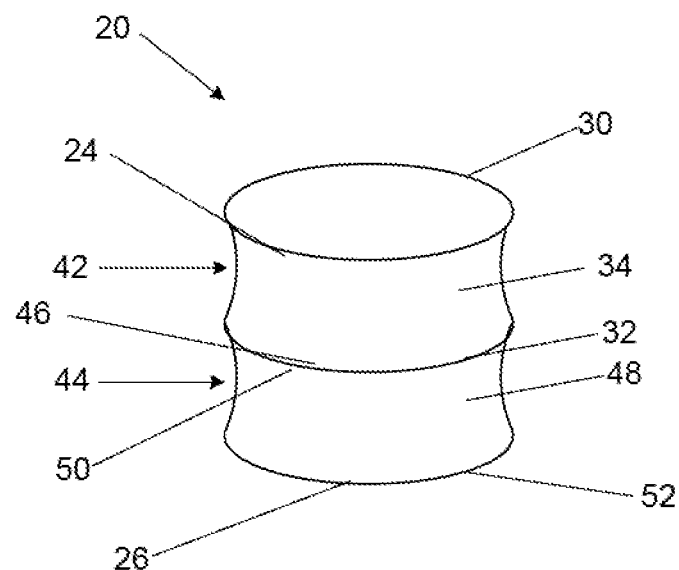

FIG. 3 illustrates an embodiment of the seal 20 that can have a first gasket 42 and a second gasket 44. Such a design can incrementally decrease the pressure across a given length so no one gasket 42 or 44 endures the entire pressure. The first gasket 42 can be similar to a single gasket seal embodiment illustrated in FIG. 2, except that the first seal cover 34 can be attached to the second seal ring 32 at a first gasket distal end 46. The second gasket 44 can have a second seal cover 48. The second seal cover 48 can be attached at a second gasket proximal end 50 to the second seal ring 32 and/or the second seal cover 48 can be integral with the first seal cover 34. The second seal cover 48 can also attach at the distal end 26 to a third seal ring 52.

Figure 4:
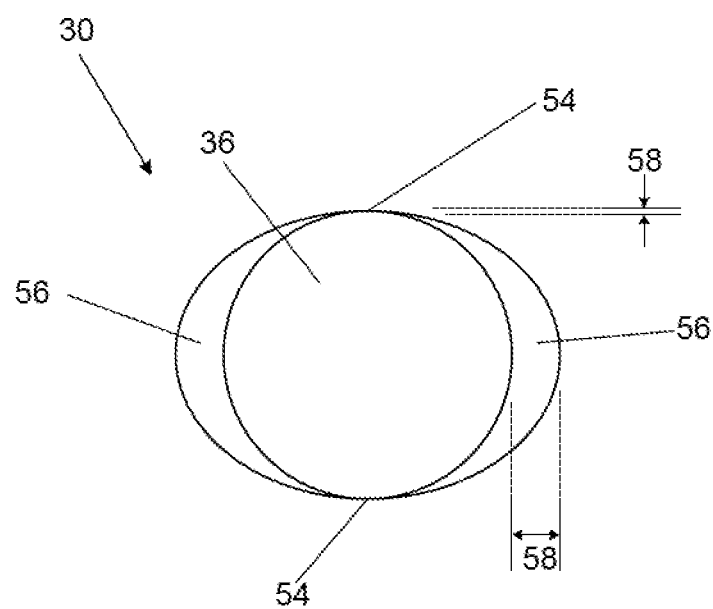
FIG. 4 is a top view of an embodiment of the seal ring.

FIG. 4 illustrates an embodiment of the seal rings 30, 32 and 52 (shown as 30). The seal ring 30 can have diametrically opposed thin sections 54 and diametrically opposed thick sections 56. The seal ring 20 can have a seal ring thickness 58 that can vary from a minimum in the thin sections 54 to a maximum in the thick sections 56. The seal ring 30 can also have a constant thickness along the entire circumference of the seal ring 30. The seal ring 30 can also have a gap in the circumference of the seal ring 30, forming a "c"-ring (not shown) as known to one having ordinary skill in the art.

Figure 5:
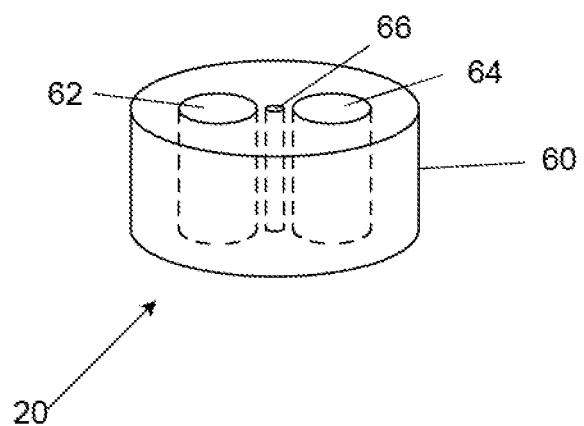
FIGS. 5-8 are front perspective views of various embodiments of the seal.

FIG. 5 illustrates an embodiment of the seal 20 that can have a seal volume 60. The seal volume 60 can be a bladder or collar filled by a fluid, for example saline, plasma, helium, oxygen, radiopaque materials (including small pieces of solids), blood, epoxy, glue, or any combination thereof. The bladder can be inflated in vivo by a method known to those having ordinary skill in the art. The seal volume 60 can also be a solid, for example polymers such as polyester (e.g., DACRON® from E. I. Du Pont de Nemours and Company, Wilmington, Del.), polypropylene, PTFE, ePTFE, PEEK, nylon, polylactic acid (PLA), poly(lactic-co-glycolic acid) (PLGA), polyglycolic acid (PGA), polyurethane, polyethylene, vascular, valvular or pericardial tissue, extruded collagen, silicone, radiopaque materials, or any combination thereof.

A first and/or second seal flow ports 62 and 64, respectively, can be defined, for example as cylinders, within the seal volume 60. Once deployed, multiple seal flow ports 62 and 64 can attach to multiple second implants 28, or multiple legs of the second implant 28 that can extend distal of the seal into the iliac arteries. A connector port 66 can also be defined, for example as a cylinder, within the seal volume 60. The second end 8 of the connector 4 can be placed into the connector port 66. The seal volume 60 can be inflated after the second end 8 is placed into the connector port 66 to constrict and pressure fit the connector port 66 around the second end 8, thereby fixedly attaching the seal 20 to the connector 4.

Figure 6:
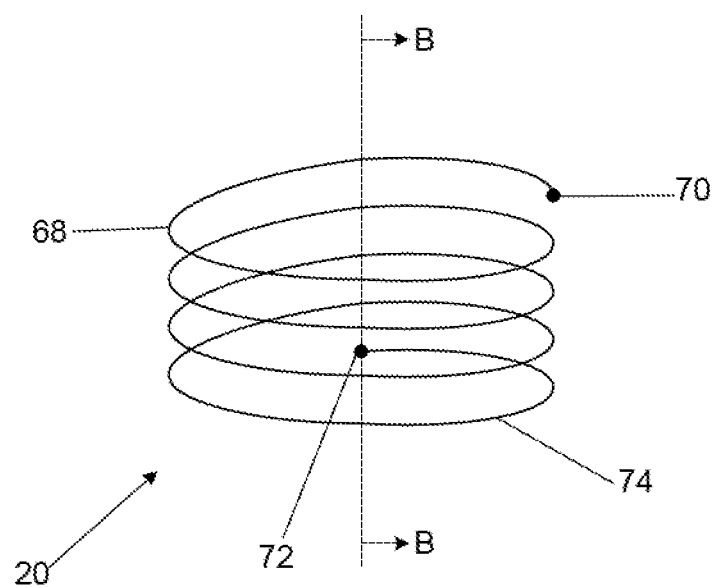

FIG. 6 illustrates an embodiment of the seal 20 that can have a helical seal coil 68 having a first end 70 and a second end 72. The ends 70 and 72 can be dulled, for example by attaching small balls as shown. The seal coil 68 can have a number of turns 74, for example from about 1.25 turns 74 to about 50 turns 74, for example about 5 turns 74.

Figure 7:
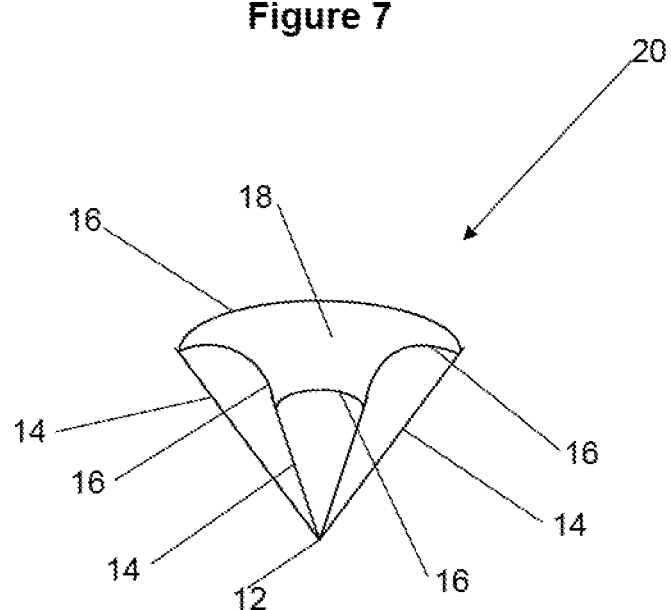

FIG. 7 illustrates an embodiment of the seal 20 that can have a structure similar to the anchor illustrated in FIG. 1 but with a vertically inverted orientation.

Figure 8:
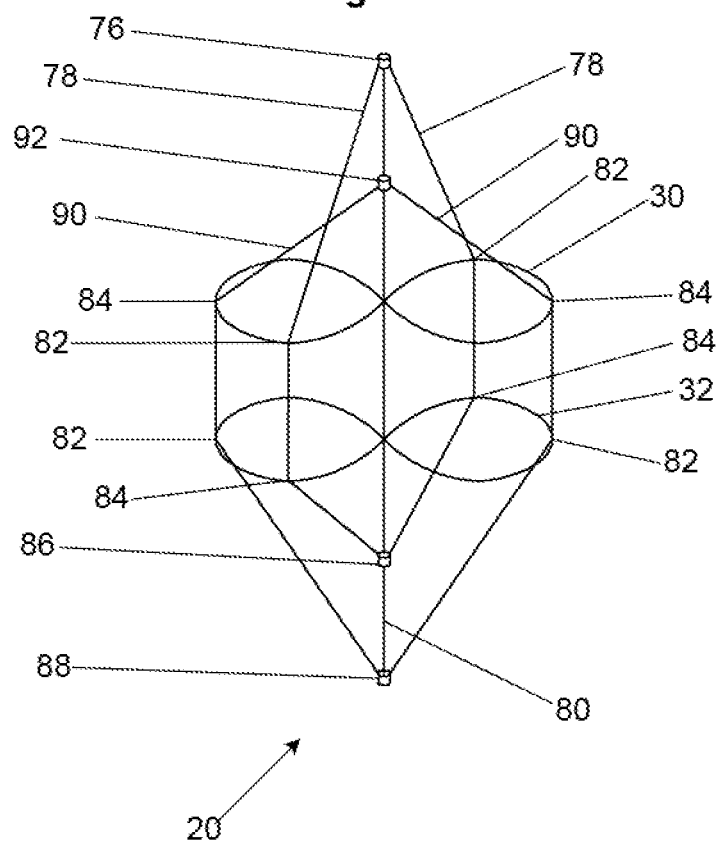

FIG. 8 illustrates an embodiment of the seal 20 that can have a first seal ring 30 and a second seal ring 32 that are mechanically insulated from each other. This structure enables the seal rings 30 and 32 to fit to more easily fit and seal an irregularly shaped vessel.

A first hub 76 can be fixedly attached or rotatably attached to first seal struts 78 and a center beam 80. The first seal struts 78 can slidably connect on the outside or inside of the first seal ring 30 at free points 82. The first seal struts 78 can be fixedly or rotatably attached to the second seal ring 32 at fixation points 84. The first seal struts 78 can be fixedly attached or rotatably attached to a first collar 86. The first collar 86 can be slidably attached to the center beam 80.

A second hub 88 can be fixedly attached or rotatably attached to second seal struts 90 and the center beam 80. The second seal struts 90 can slidably connect on the outside or inside of the second seal ring 32 at the free points 82. The second seal struts 90 can be fixedly or rotatably attached to the first seal ring 30 at the fixation points 84. The second seal struts 90 can be fixedly attached or rotatably attached to a second collar 92. The second collar 86 can be slidably attached to the center beam 80. The seal struts 78 and 90, the hubs 76 and 88, and the collars 86 and 92 can be from the same materials as the seal rings 30, 32 and 52.

Figure 9:
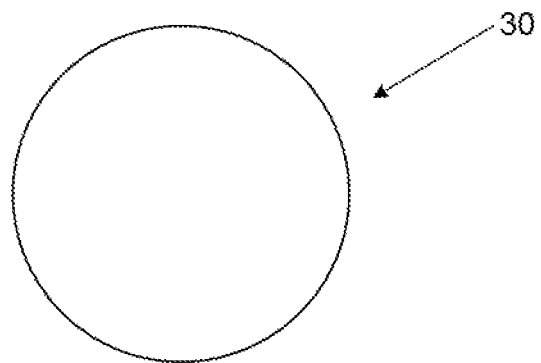
FIGS. 9 and 10 are a top and a side view, respectively, of the embodiment of the seal ring shown in FIG. 8.
Figure 10:
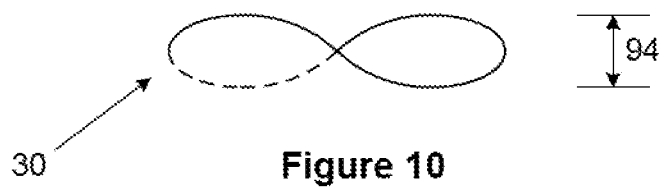

The seal rings 30 and 32 can be wave-shaped. FIG. 9 illustrates a top view of one embodiment of the wave-shaped seal ring 30, showing a circular shape from above. FIG. 10 illustrates a side view of the wave-shaped seal ring 30 illustrated in FIGS. 8 and 9, showing two periods of smooth oscillation in a seal ring height 94.

Figure 11:
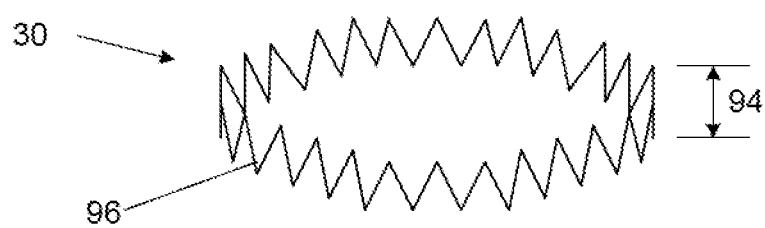
FIGS. 11 and 12 are front perspective views of various embodiments of the seal ring.
Figure 12:
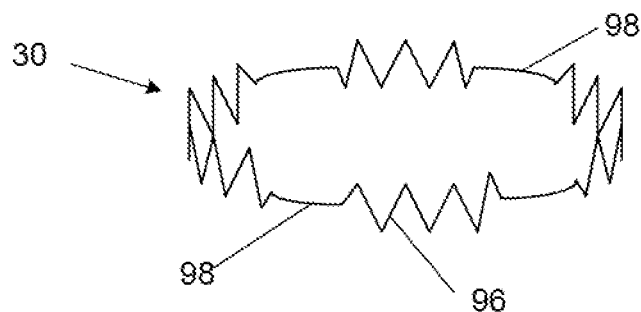

FIG. 11 illustrates an embodiment of the seal ring 30 that can have sharp oscillations in the seal ring height 94. Angled seal ring struts 96 can form the seal ring 30 into a zigzag. FIG. 12 illustrates a seal ring 30 that can have a combination of alternating lock zones 98 and angled seal ring struts 96. The lock zones 98 can be substantially parallel to the circumference of the seal ring 30.

FIG. 13 illustrates an embodiment of cross-section A-A (shown in FIG. 1) of the intravascular implant 2 without the seal 20. The anchor 10 can have connectors 4 attached to the arms 14. The second end 8 of each connector 4 can have an integral attachment device 22. The attachment device 22 can be made of a slide 100 and an interference piece 102 defining a catch 104 there between. The slide 100 can have a slide angle 106 from about 90° to about 180°. The slide 100 can also have a slide height 108 from about 0.38 mm (0.015 in.) to about 6.35 mm (0.250 in.), for example about 3.18 mm (0.125 in.). The interference piece 102 can have an interference piece depth 110 from about 0.38 mm (0.015 in.) to about 4.95 mm (0.195 in.). The slide 100 and interference piece 102 can be from the same materials as the seal rings 30, 32 and 52 or seal covers 34 and 48.

FIG. 14 illustrates an embodiment of the intravascular implant 2. The anchor 10 can have a solid ring, and can be fixedly or rotatably attached to about two or more connectors 4. The seal ring 30 can be vertically surrounded by the slides 100 and the interference pieces 102. The seal ring 30 can, therefore, be engaged in the catch 104 and fixedly attached to the connectors 4.

Figure 15:
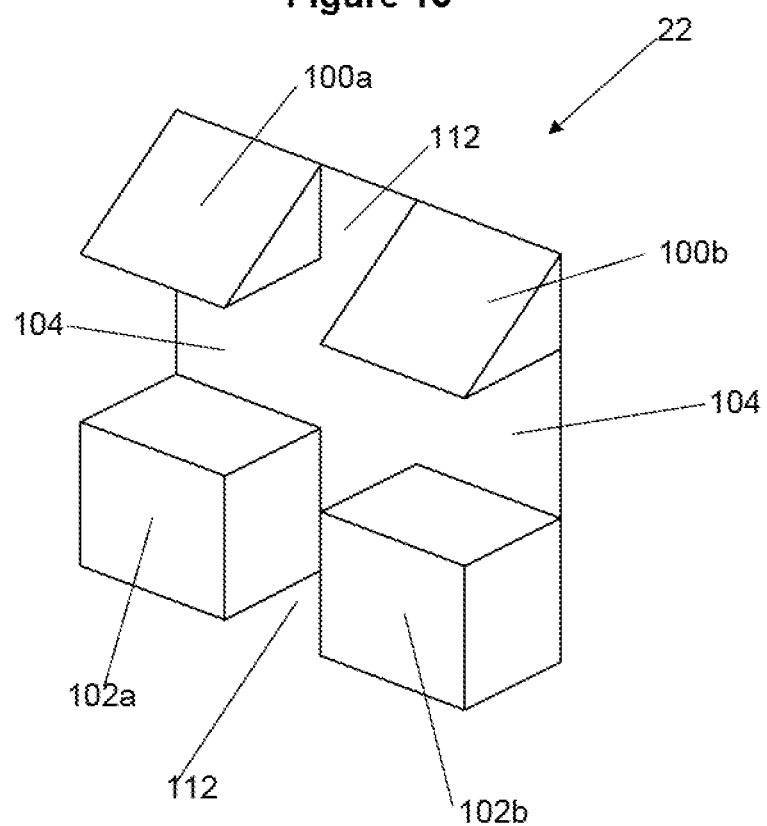
FIG. 15 is a perspective view of an embodiment of the attachment device.

FIG. 15 illustrates an embodiment of the attachment device 22. The attachment device 22 can have first and second slides 100*a* and 100*b*, first and second interference pieces 102*a* and 102*b*, a catch 104 defined by the slides 100*a* and 100*b* and the interference pieces 102*a* and 102*b*. The attachment device 22 can also have a rod slot 112 defined between the first slide 100*a* and second slide 100*b*, and between the first interference piece 102*a* and the second interference piece 102*b*.

Figure 16:
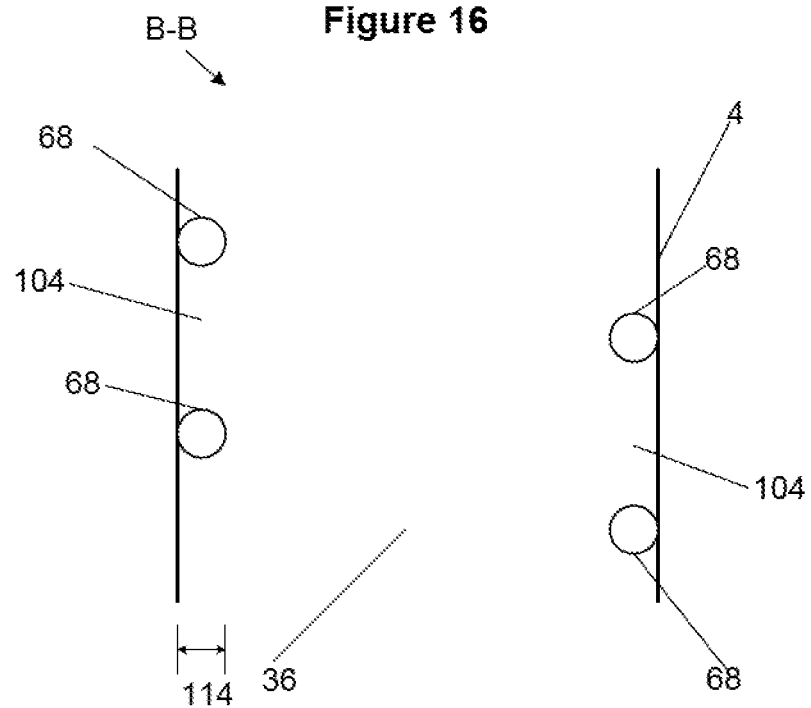
FIG. 16 illustrates an embodiment of cross-section B-B of the seal with the connectors.

FIG. 16 illustrates an embodiment of cross-section B-B (shown in FIG. 6) of the seal 20. The two turns of the coil 68 can define the catch 104. The coil 68 can have a coil wire diameter 114 from about 0.03 mm (0.001 in.) to about 1.3 mm (0.050 in.), for example about 0.64 mm (0.025 in.).

Figure 17:
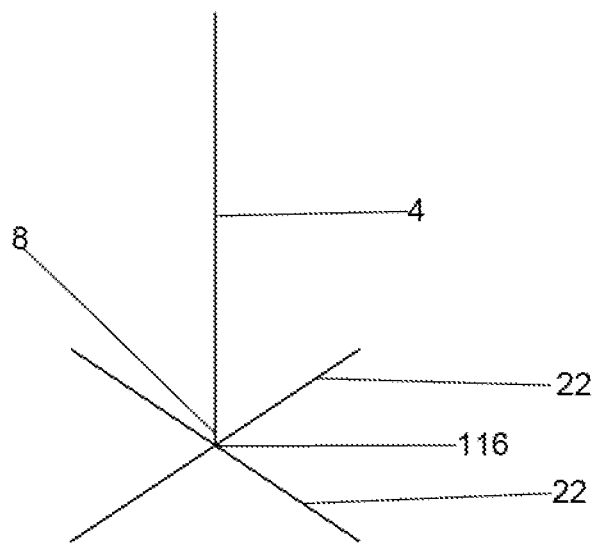
FIG. 17 is a front perspective view of an embodiment of the connector and the attachment device.

FIG. 17 illustrates an embodiment of the connector 4 that can be attached to the attachment devices 22, that can be, in turn, attached to the seal 20. The connector 4 can be a flexible wire, coil, rod or combinations thereof and can be hollowed. The connector 4 can also be threaded to rotatably fit the anchor 10 and seal 20 or attachment device 22. The connector can be made from any material listed for the anchor 10.

The attachment devices 22 can be wires, coils, rods or combinations thereof. The connector 4 can also be directly attached to the seal 20. The connector 4 can be attached to the attachment devices 22 at a connector interface 116. The connector interface 116 can have a hub, slider, or collar. The connector interface 116 can be a direct attachment. The connector 4 and attachment device 22 can also be an integral part. The seal 20 and attachment device 22 can also be an integral part.

Figure 18:
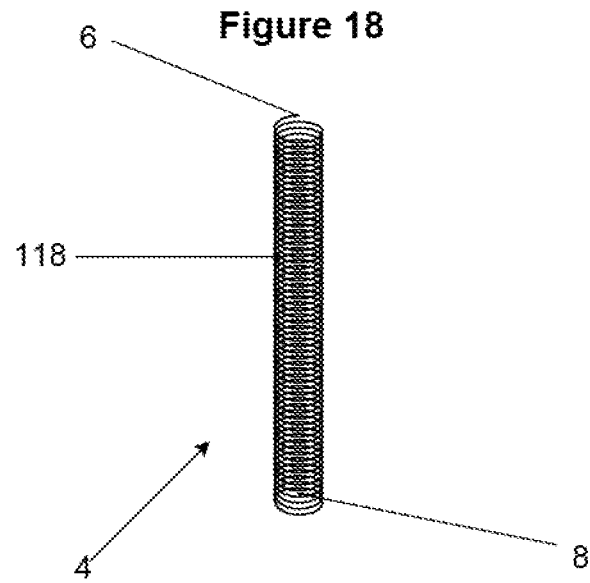
FIGS. 18-20 illustrate embodiments of the connector.
Figure 19:
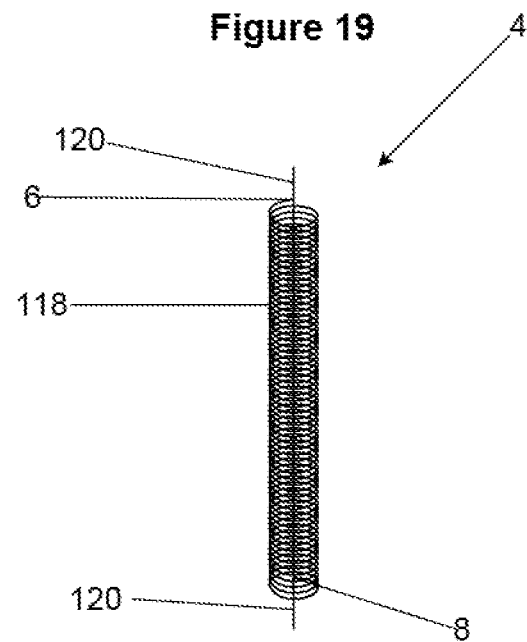
Figure 20:
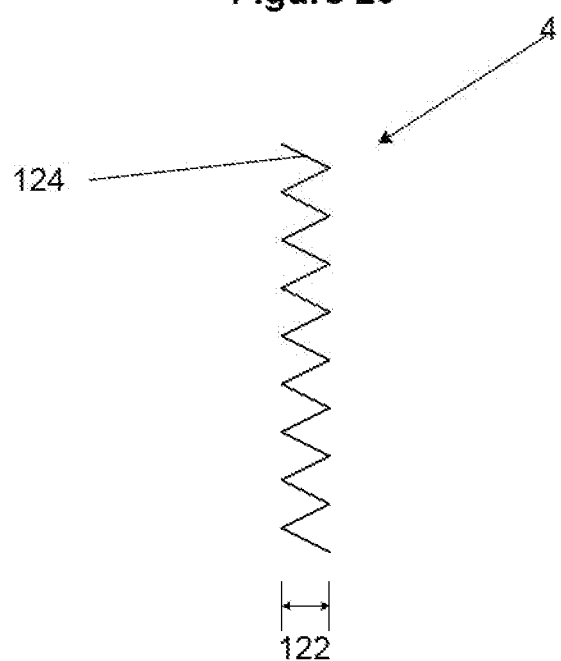

FIG. 18 illustrates an embodiment of the connector 4 that can be made from a helical connector coil 118. The connector coil 118 can be made from a wire, for example a guidewire, having a diameter from about 0.46 mm (0.018 in.) to about 2.54 mm (0.100 in.). FIG. 19 illustrates an embodiment of the connector 4 that can be made from the connector coil 118 and a connector wire or rod 120. The connector wire or rod 120 can also be made from a wire, for example a guidewire, having a diameter from about 0.46 mm (0.018 in.) to about 2.54 mm (0.100 in.). FIG. 20 illustrates an embodiment of the connector 4 that can have sharp oscillations in connector width. Angled connector struts 124 can form the connector 4 into a zigzag.

Figure 21:
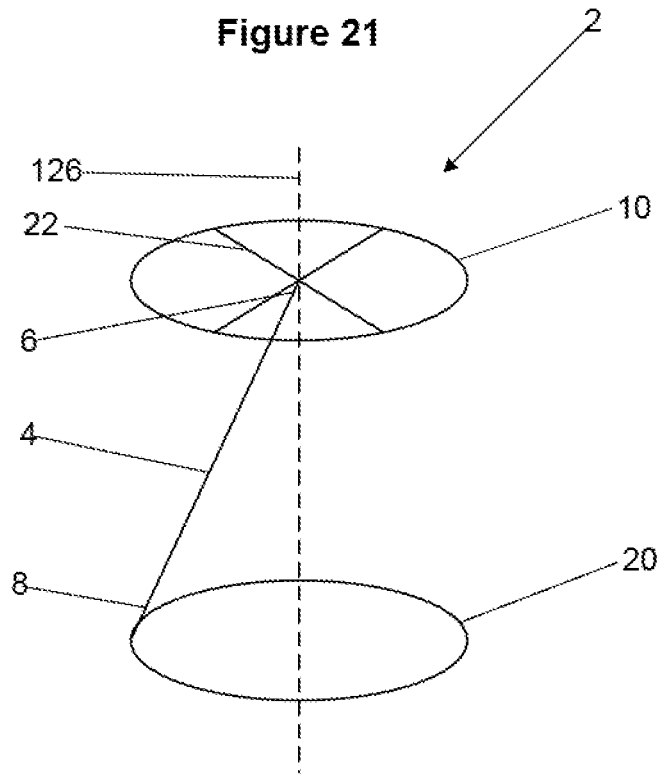
FIGS. 21-23 are front perspective views of various embodiments of the intravascular implant.

FIG. 21 illustrates an embodiment of the intravascular implant 2 that can a longitudinal axis 126. The attachment device 22 can attach the connector 4 to the anchor 10 such that the first end 6 can be substantially on the longitudinal axis 126. The second end 8 can attach to the seal 20 substantially along a radial perimeter of the seal 20.

Figure 22:
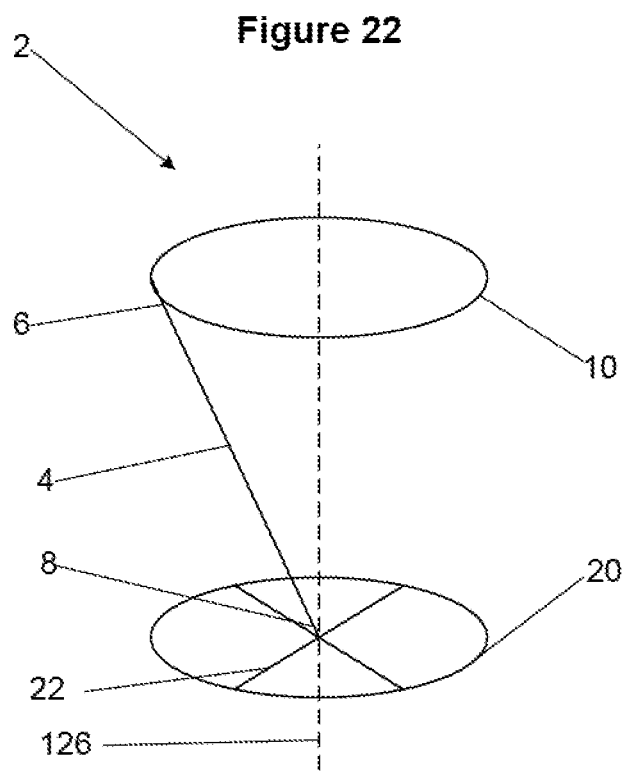

FIG. 22 illustrates an embodiment of the intravascular implant 2 that can have the attachment device 22 attach the connector 4 to the seal 20 such that the second end 8 can be substantially on the longitudinal axis 126. The first end 6 can attach to the anchor 10 substantially along a radial perimeter of the anchor 10.

Figure 23:
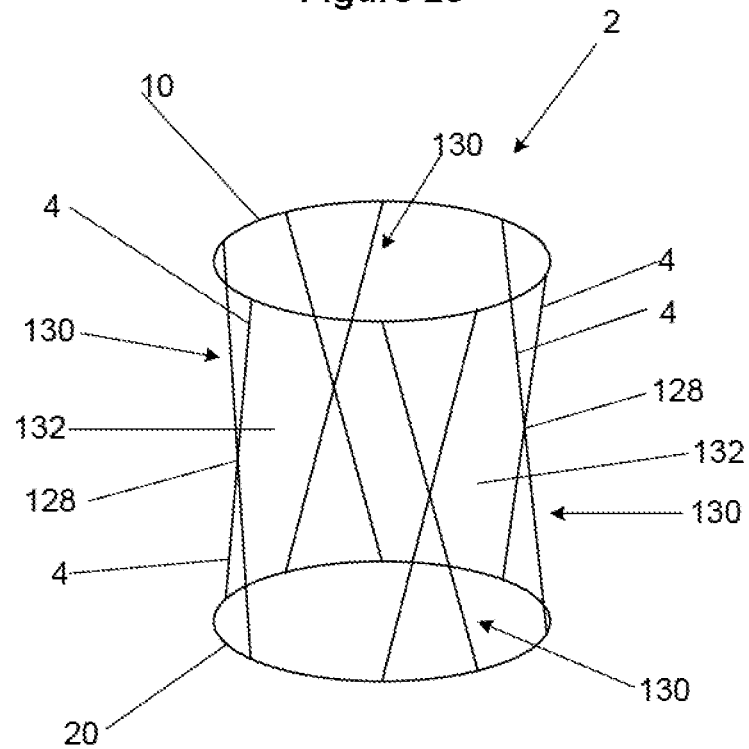

FIG. 23 illustrates an embodiment of the intravascular implant 2 that can have multiple connectors 4. The connectors 4 can rotatably or fixedly attach to each other near their centers at joint points 128. Joined pairs of connectors 4 can form x-beams 128. The x-beams 128 can define transverse flow ports 132.

Figure 24:
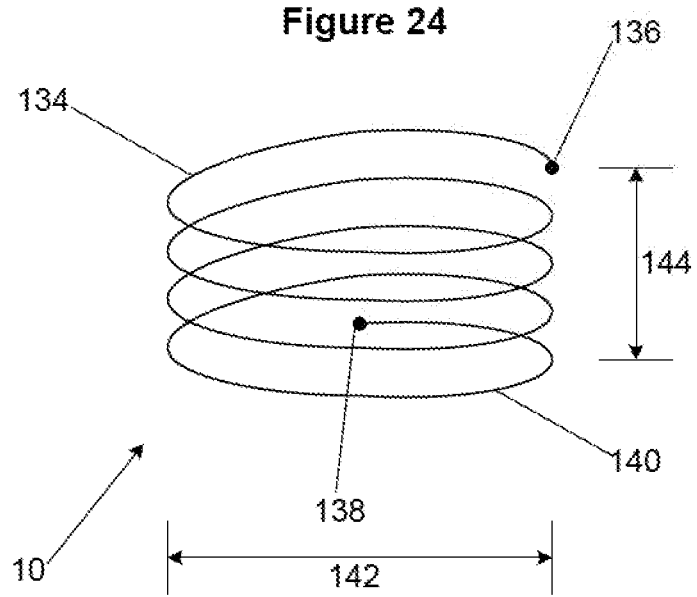
FIGS. 24 and 25 are front perspective views of various embodiments of the anchor.

FIG. 24 illustrates an embodiment of the anchor 10 shaped as a helical anchor coil 134 having a first end 136 and a second end 138. The ends 136 and 138 can be dulled, for example by attaching small balls as shown. The seal coil 134 can have from about 1 turn 140 to about 10 turns 140, for example about 4 turns 140. The anchor 10 can also have an anchor width 142 from about 5 mm (0.2 in.) to about 50 mm (2 in.). The anchor 10 can also have an anchor height 144.

Figure 25:
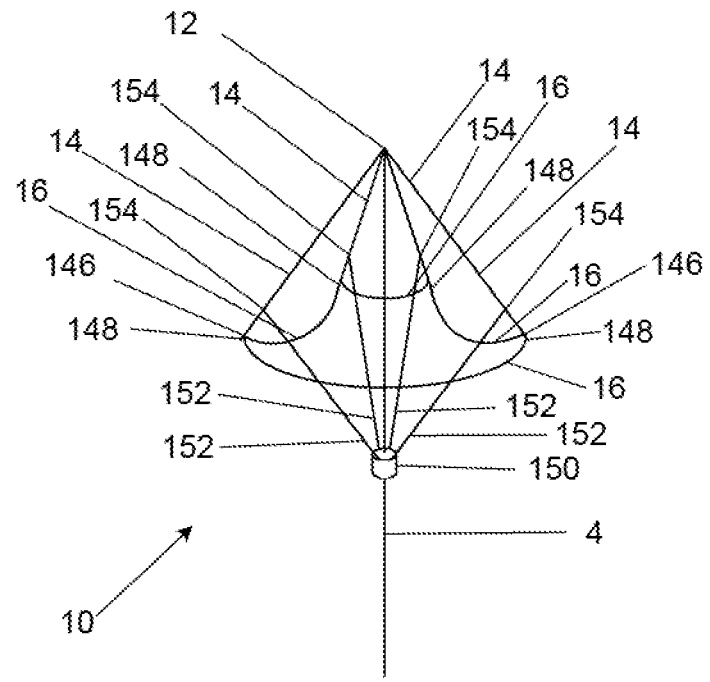

FIG. 25 illustrates an embodiment of the anchor 10. The anchor 10 can have the central tip 12, the arms 14, and the leaves 16 as shown and described in FIG. 1. The arms 14 can also extend radially beyond each attachment point 146 of each arm 14 and each leaf 16 to form a diminishing spring force element or tissue mainstay 148. The spring force elements or tissue mainstays 148 on the anchor 10 can be the same material and design as the tissue mainstays 33 on the seal 20, and vice versa. Anchor collar 150 can be slidably mounted to the connector 4 to radially extend or contract the arms 14 and to adjust the height between the anchor 10 and the seal 20 to better place the implant 2 with regard to the transverse vessels, for example the renal arteries, and vascular wall abnormalities. The anchor collar 150 can be fixedly or rotatably attached to arm supports 152. The arm supports 152 can be fixedly or rotatably attached to the arms 14 at support points 154. The arm supports 152 can also be an integral part of the anchor collar 150 and/or the arms 14. The central tip 12, arms 14, leafs 16, mainstays 148, and arm supports 152 can be made from the same materials listed for the seal rings 30, 32 and 52.

Figure 26:
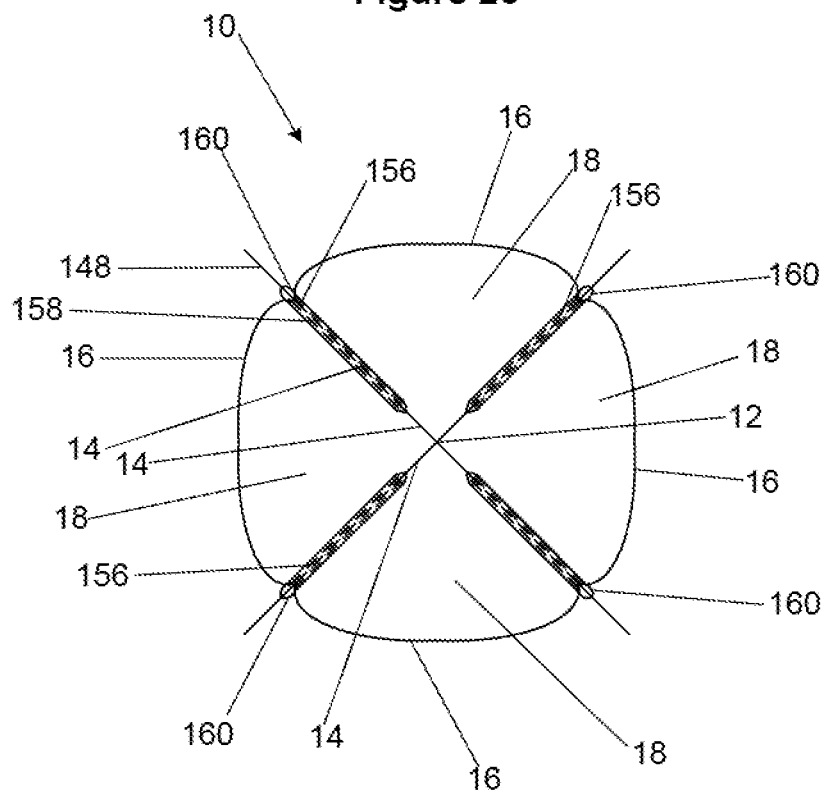
FIG. 26 is a top view of an embodiment of the anchor.

FIG. 26 illustrates a top view of an embodiment of anchor 10. Each leaf 16 can have a first leaf end 156 and a second leaf end 158. The first leaf end 156 of one leaf 16 can merge with the second leaf end 158 of the neighboring leaf 16 and the intermediate arm 14 into a cover 160. The cover 160 can be a cylinder with two open ends. The leaf 16, first leaf end 156, second leaf end 158 and cover 160 can be fixedly or rotatably attached. The first leaf end 156 and the second leaf end 158 can terminate within the cover 160. When deployed, the leaf 16 can press against the vascular wall to maintain a substantially circular cross-section of the vessel.

Figure 27:
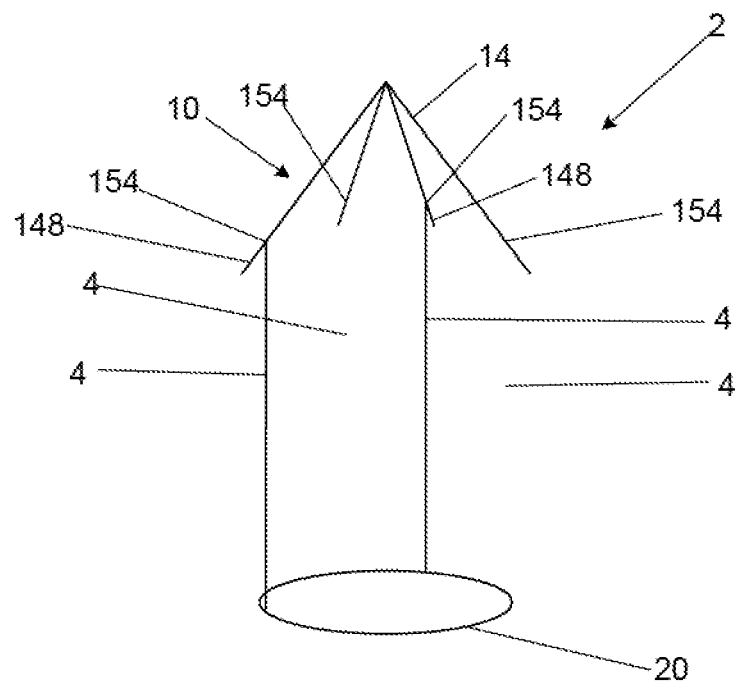
FIGS. 27-29 illustrate various embodiments of the intravascular implant.
Figure 28:
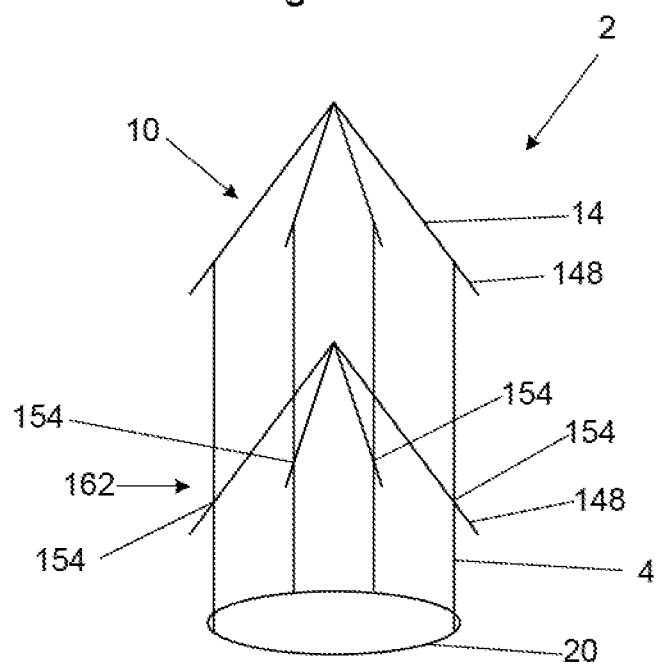
Figure 29:
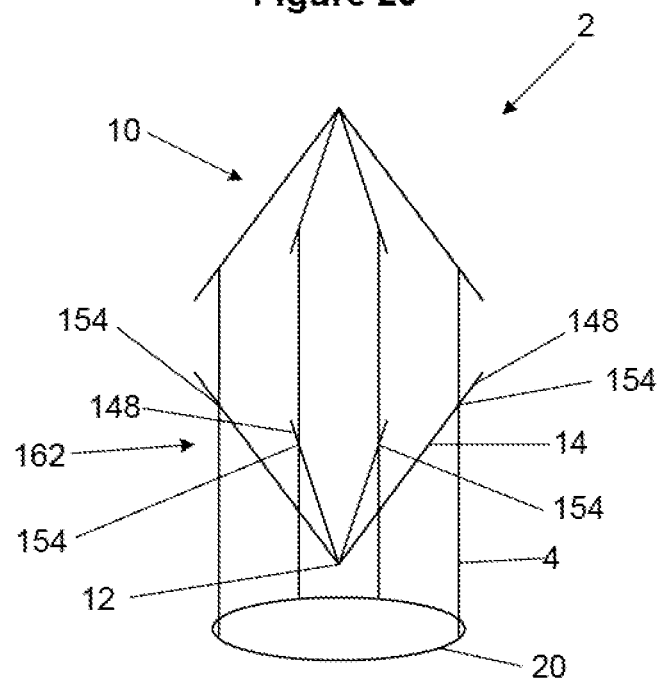

FIG. 27 illustrates an embodiment of the intravascular implant 2 having the arms 14 supported at support points 154 by the connectors 4. The seal 20 can also be radially collapsible and expandable. FIGS. 28 and 29 illustrate embodiments of the intravascular implant 2 that can have a first anchor 10 and a second anchor 162. The second anchor can be fixedly or rotatably attached to connectors 4 at support points 154. The second anchor 162 can also be vertically inverted with respect to the first anchor, as shown in FIG. 29.

Methods of Manufacture

The tissue mainstays 33, shown in FIG. 2, can be directly attached to the seal rings 30, 32 or 52 by, for example, melting, screwing, gluing, welding or use of an interference fit or pressure fit such as crimping, or combining methods thereof, to join the connector 4 to the seal 20. The tissue mainstays 33 and the seal rings 30, 32 or 52 can be integrated, for example, by die cutting, laser cutting, electrical discharge machining (EDM) or stamping from a single piece or material. The connector interface 116, shown in FIG. 17, can also directly attach to the connector 4 and the seal 20 or be integrated thereto by any method listed for the tissue mainstays 33 and the seal rings 30, 32 or 52. The arm supports 152, shown in FIG. 25, can also be integrated with the anchor collar 150 and/or the arms 14 by any method listed for the tissue mainstays 33 and the seal rings 30, 32 or 52. As shown in FIG. 26, the leaf 16, first leaf end 156, second leaf end 158 and cover 160 can be fixedly or rotatably attached or integrally formed by any by any method listed for the tissue mainstays 33 and the seal rings 30, 32 or 52.

As shown in FIG. 19, the connector coil 118 and connector rod 120 can be attached at the first connector end 6 and the second connector end by methods known to one having ordinary skill in the art.

Integrated parts can be made from pre-formed resilient materials, for example resilient alloys (e.g., Nitinol, ELGILOY®) that are preformed and biased into the post-deployment shape and then compressed into the deployment shape.

Any elongated parts used in the intravascular implant 2 and the second implant 28, for example the tip 12, the arms 14, the leafs 16, the attachment devices 22, the seal rings 30, 32 and 52, the seal coil 68, the connector coil 118, the connector rod 120, the connector strut 124, the anchor coil 134 and the arm supports 152, can be ovalized, or have an oval cross section where necessary, to ease crimping with other parts.

Method of Use

Figure 30:
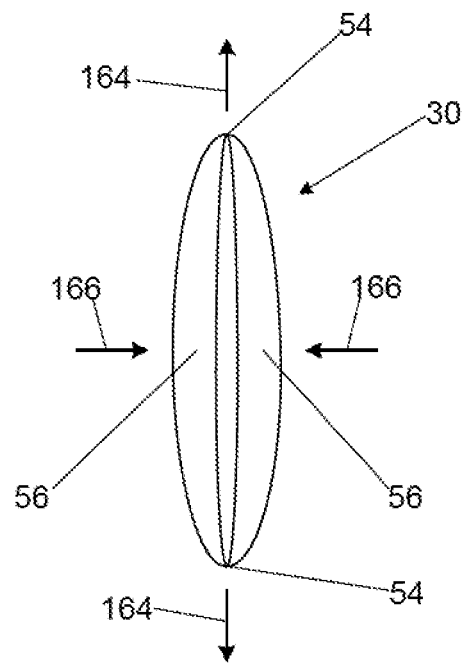
FIG. 30 illustrates an embodiment of a method for compressing the seal ring for deployment.

The intravascular implant 2 can be collapsed or compressed into a deployment configuration to enable minimally invasive implantation into the vasculature of a patient. FIG. 30 illustrates one embodiment of compressing the seal ring 30, as shown in FIG. 4, by applying outward radial forces, as shown by arrows 164, to the thin sections 54 and/or by applying an inward radial force, as shown by arrows 166, to the thick sections 56. Other embodiments can be compressed by applying inward radial forces spread around the circumference of the implant and/or other methods known to those having ordinary skill in the art.

Figure 31:
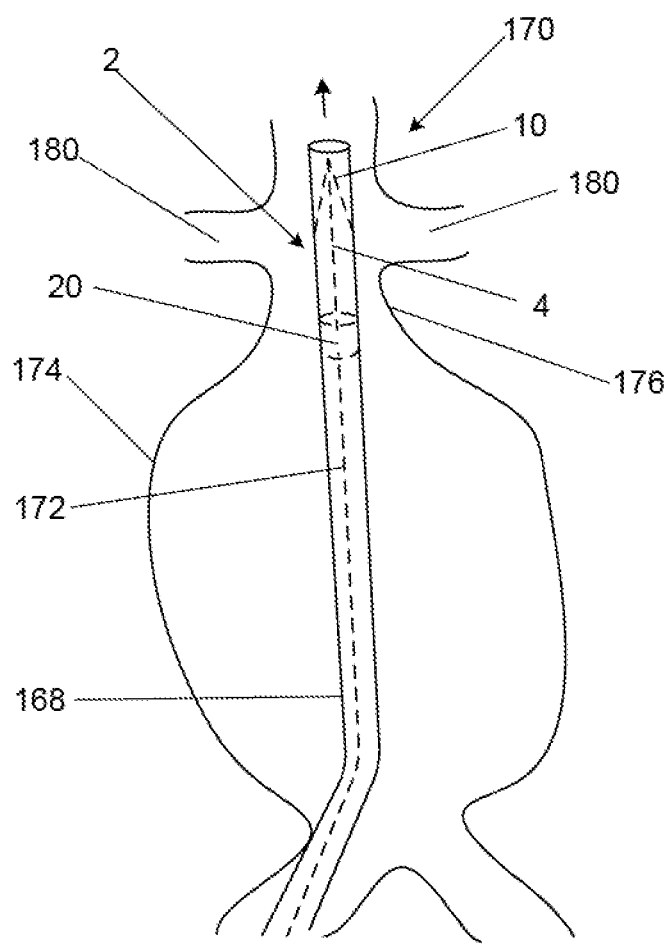
FIGS. 31-33 illustrate an embodiment of a method for deploying the intravascular implant into a vascular site.

The intravascular implant 2 can be loaded into a delivery catheter 168 by methods known to those having ordinary skill in the art. Because the design of the intravascular implant 2 can separate the anchor 10 from the seal 20, a low profile catheter can be used to deliver the intravascular implant 2. As illustrated in FIG. 31, the delivery catheter 168 can be positioned, as shown by the arrow, at a vascular site 170 using a guidewire (not shown) and an "over-the-wire" delivery method, known to those having ordinary skill in the art. A control line 172 can also extend distally from the implant 2. The control line 172 can include controls used to manipulate any part of the intravascular implant 2 such as rotating the seal 20, expanding or contracting the arms 14, or separating delivery devices from the implant 2, and/or to deliver a substance such as a medication or radiopaque material, and/or to receive signals such as optical or electrical signals. The vascular site 170 can be adjacent to a vascular aneurysm 174, for example an abdominal aortic aneurysm, having a proximal neck 176 and transverse vessels 180, for example renal arteries, proximal to the vascular aneurysm 174.

Figure 32:
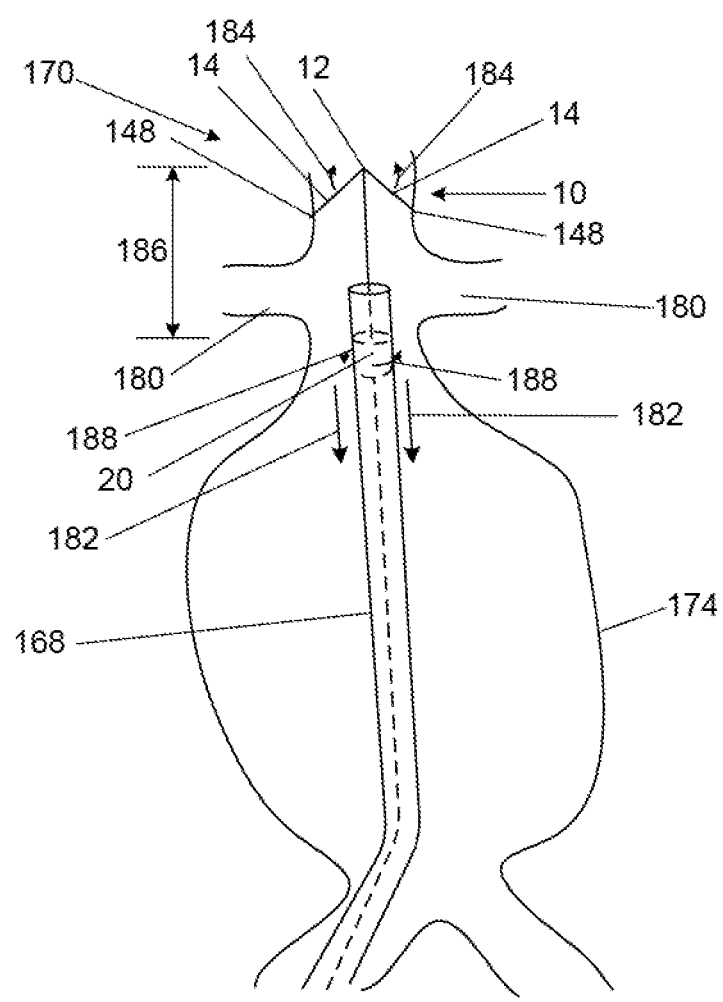

FIG. 32 illustrates that the catheter 168 can be partially distally retracted, as shown by arrows 182, thereby exposing the arms 14 while retaining the seal 20. Once exposed, the arms 14 can expand radially, as shown by arrows 184. Expansion of the arms 14 can occur due to resilient material expansion or mechanical manipulation. The tissue mainstays 148 can seat in the wall of the vascular site 170 proximal to the transverse vessels 180, preventing the anchor 14 from moving distally. Multiple, independent arms 14 can adjust to the surrounding vasculature geometry to fit as needed for secure attachment to the vascular wall. The distance between the central tip 12 and the seal 20 can be an effective connector length 186. The effective connector length 186 can be adjusted after the tissue mainstays 148 have been seated in the wall of the vascular site 170. The effective connector length 186 can be adjusted by rotating the seal 20, as shown by arrows 188, along a threaded connector 4.

Figure 33:
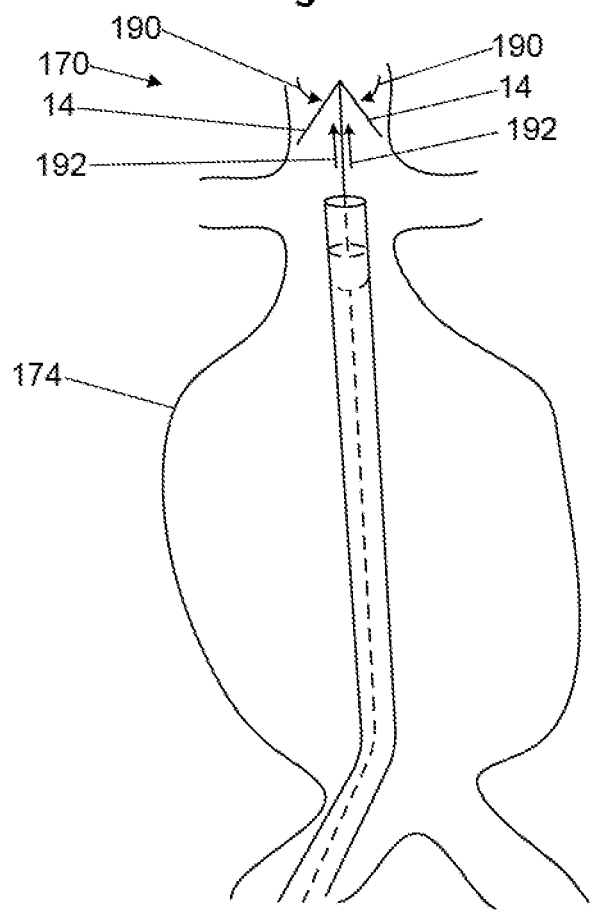

FIG. 33 illustrates that the arms 14 can be contracted, as shown by arrows 190. The anchor 10 can then be easily repositioned, as shown by arrows 192. The intravascular implant 2 can be made from or combined with radiopaque materials and markers to aid the placement, adjustments and repositioning of the intravascular implant 2 and associated parts with the use of an angiogram.

Figure 34:
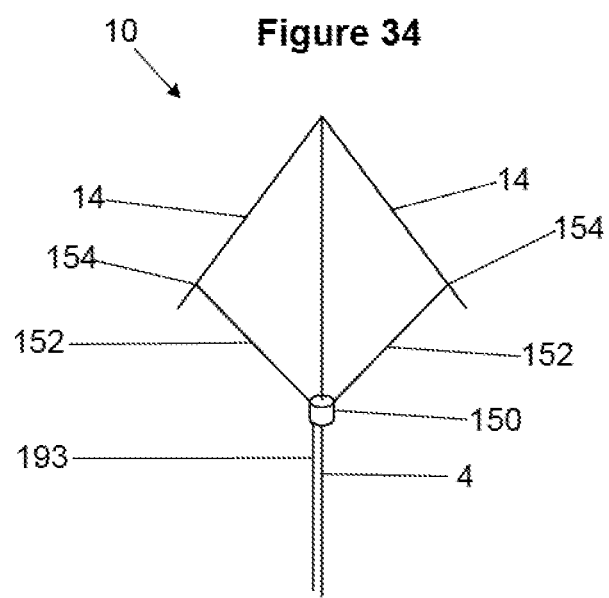
FIGS. 34-37 illustrate various embodiments of radially contracting and expanding the anus of the anchor.
Figure 35:
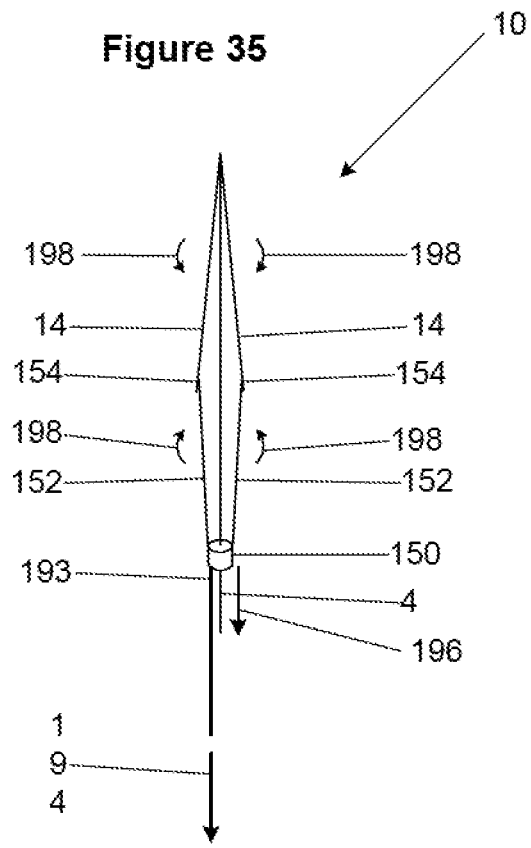

FIG. 34 illustrates an embodiment of the connector 4 and the anchor 10 that can have a contraction line 193 releasably connected to the anchor collar 150. Contraction line 193 can be formed of coaxial hypotubes. Contraction line 193 can also be part of control line 172. The arms 14 can be biased to radially expand or radially contract. FIG. 35 illustrates that the contraction line 193 can be pulled, as shown by arrow 194, which can result in a distal movement of the anchor collar 150, as shown by arrow 196. The distal movement of the anchor collar 150 can cause the arm supports 154 and, in turn, the arms 14 to rotate inward and radially contract, as shown by arrows 198. The above process can be reversed and the arms 14 can be radially expanded. The contraction line can be separated from the anchor collar 150 when placement of the anchor 10 is finalized.

Figure 36:
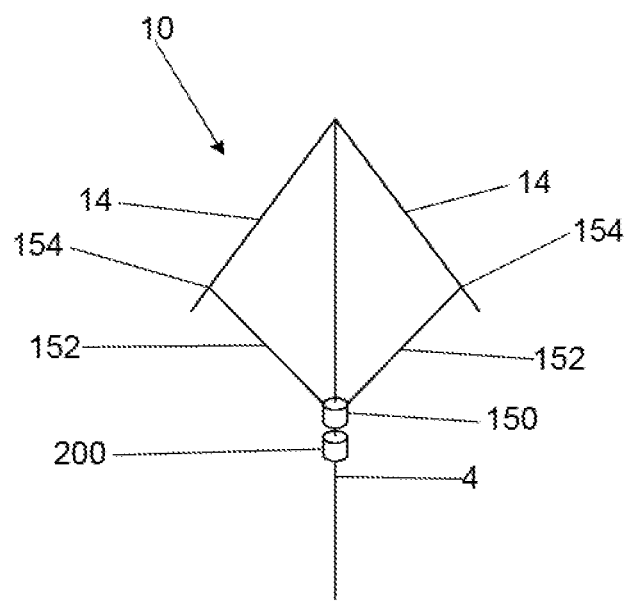
Figure 37:
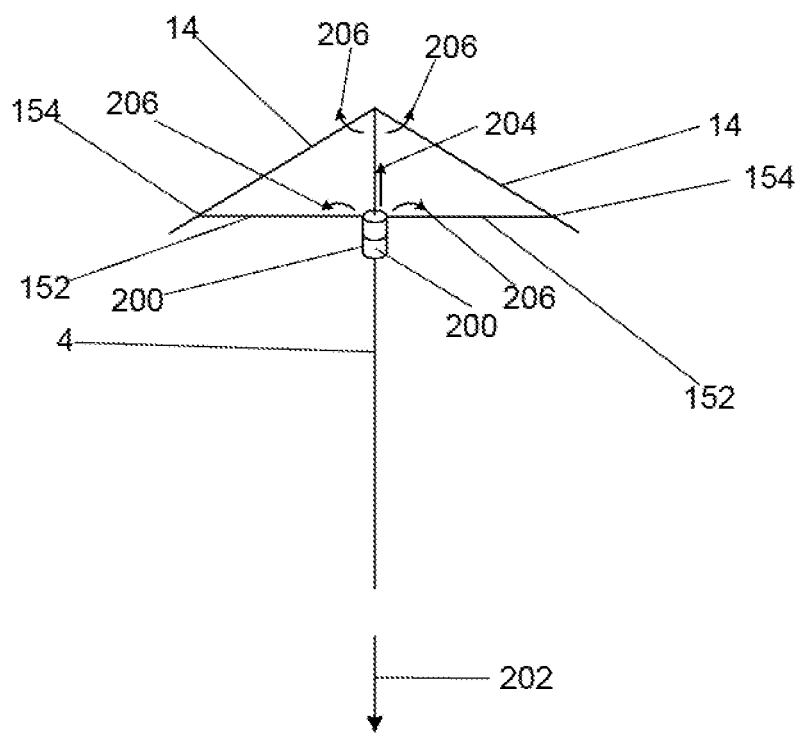

FIG. 36 illustrates an embodiment of the connector 4 and the anchor 10 that can have a fixed hub 200 that is fixedly held in space, for example by the seal 20, the delivery catheter 168 and/or the control line 172, distal to the anchor collar 150. The fixed hub 200 can also be slidably connected to the connector 4. FIG. 37 illustrates that the connector 4 can be pulled distally, as shown by arrow 202, which can cause the anchor collar 150 to butt against the fixed hub 200 and be forced proximally with respect to the connector 4, as shown by arrow 204. The proximal movement of the anchor collar 150 can cause outward rotation and radial expansion of the arm supports 154 and, in turn, the arms 14, as shown by arrows 206. The above process can be reversed and the arms 14 can be radially contracted. The arms 14 can be locked into place by methods known to those having ordinary skill in the art.

Figure 38:
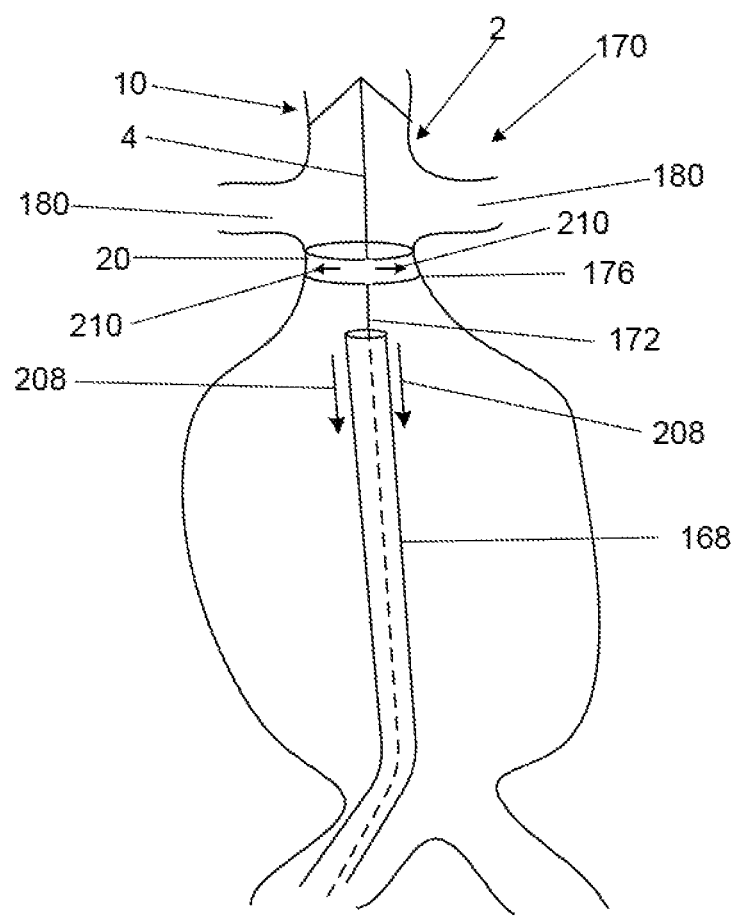
FIG. 38 illustrates an embodiment of a method for deploying the intravascular implant into a vascular site.

FIG. 38 illustrates that the catheter 168 can be retracted distally of the seal 20, as shown by arrows 208. Retracting the catheter 168 can expose the seal 20, allowing the seal 20 to radially expand, as shown by arrows 210. The seal 20 can be placed to seat in the proximal neck 176. When fully deployed, the intravascular implant 2 can have an open-walled structure, and can therefore be placed adjacent to the transverse vessels 180 without interfering with the flow through the transverse vessels 180.

Figure 39:
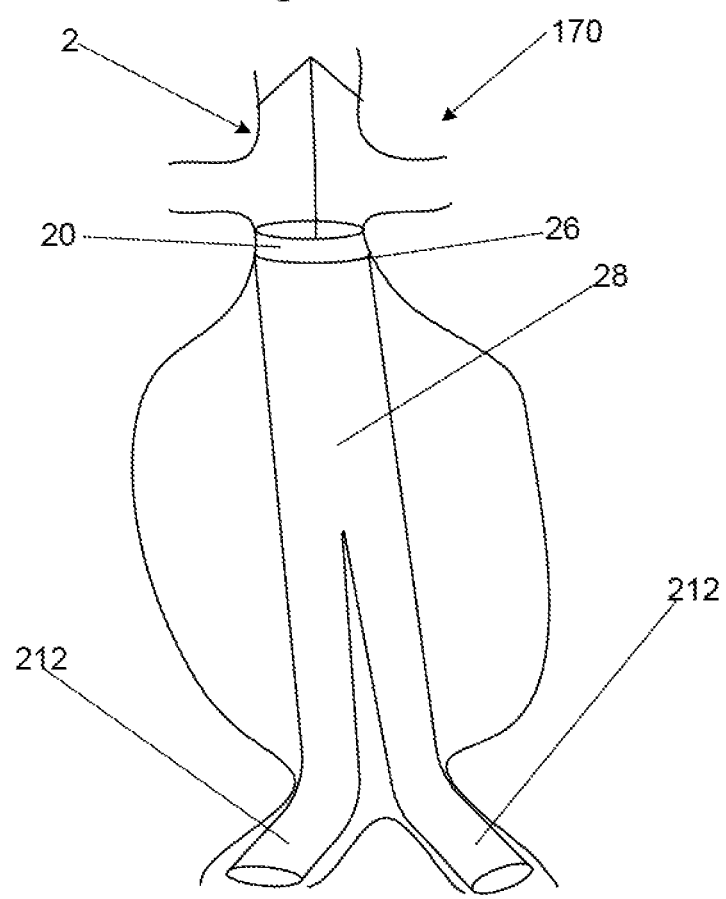
FIG. 39 illustrates an embodiment of a method for deploying the second implant with the intravascular implant.

FIG. 39 illustrates the intravascular implant 2 that can be implanted in the vascular site 170. The distal end 26 can be attached to a second implant 28, for example a vascular graft such as an abdominal aortic aneurysm graft, for example a gel weave aortic graft. The second implant 28 can have two branching legs 212.

Figure 40:
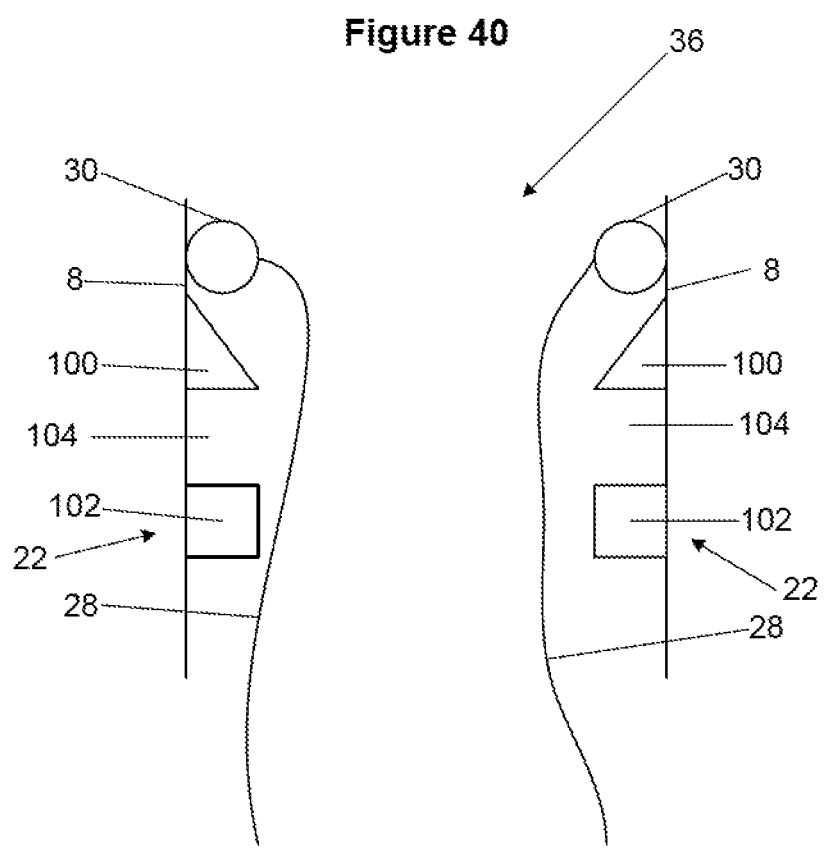
FIGS. 40-42 illustrate an embodiment of a method for attaching the seal to the attachment device.
Figure 41:
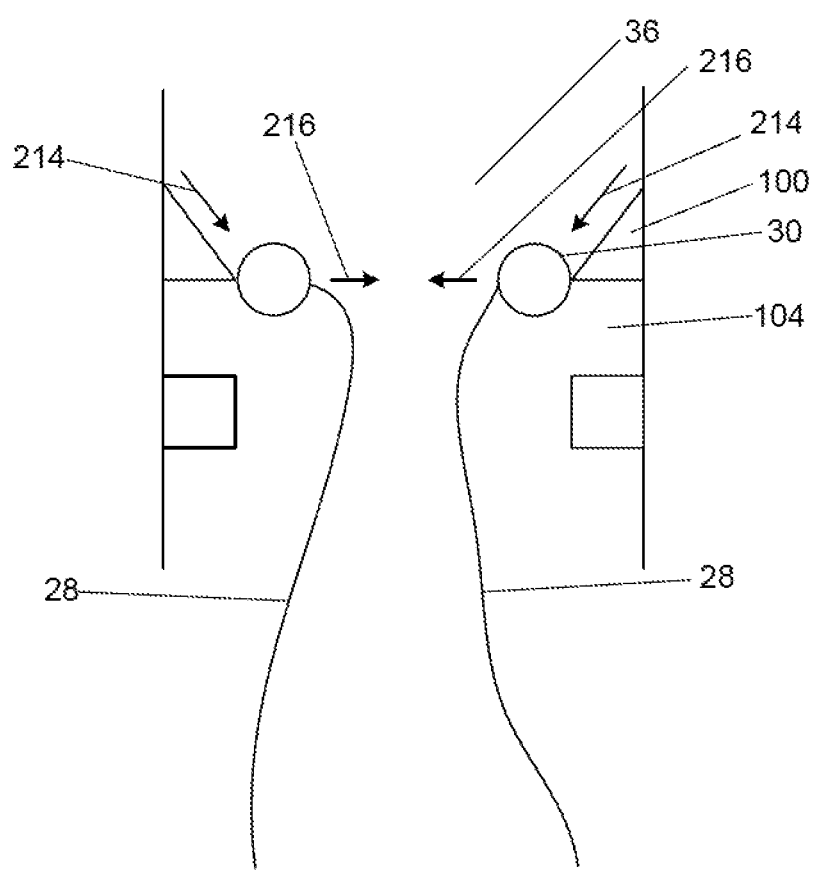
Figure 42:
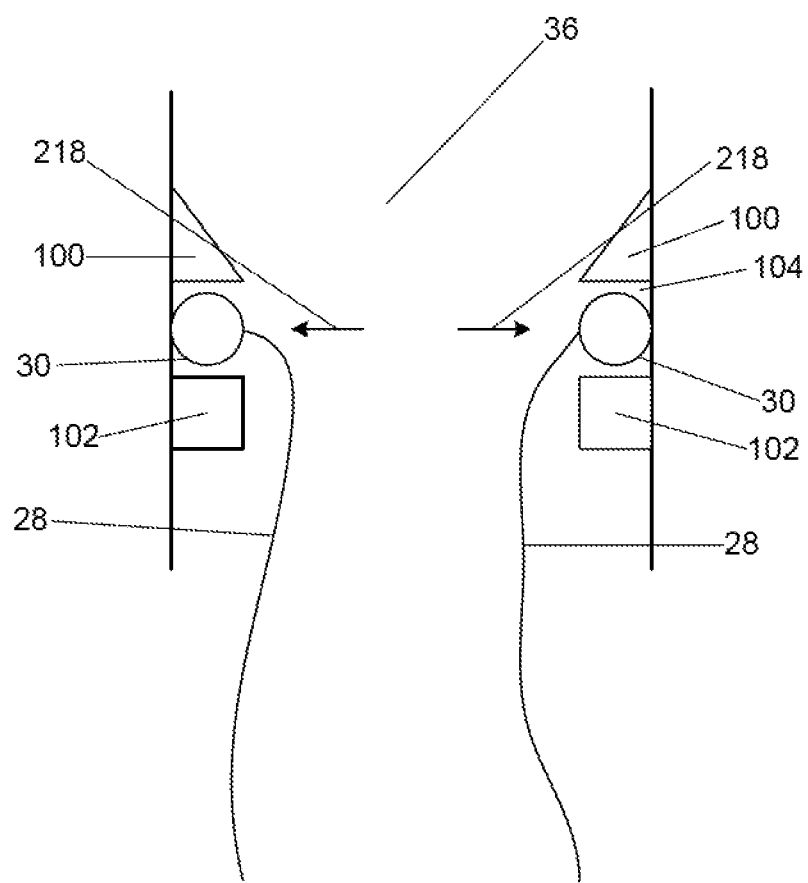

FIG. 40 illustrates a cross-section of an embodiment of the attachment device 22 and second end 8 of the seal 20. The seal ring 30 can be proximal to the slides 100. The seal cover 34 or the second implant 28 can extend from the seal ring 30. FIG. 41 illustrates pulling the seal ring 30 along the slides 100, as shown by arrows 214. Movement of the seal ring 30 along the slides 100 can cause the seal ring to radially contract, as shown by arrows 216. Once the seal ring 30 is distally clear of the slides 100, the seal ring 30 can radially expand, as shown by arrows 218, and seat into the catch 104. Once in the catch 104, the seal ring 30 can be held vertically in place by the distal side of the slide 100 and the proximal side of the interference piece 102.

Figure 43:
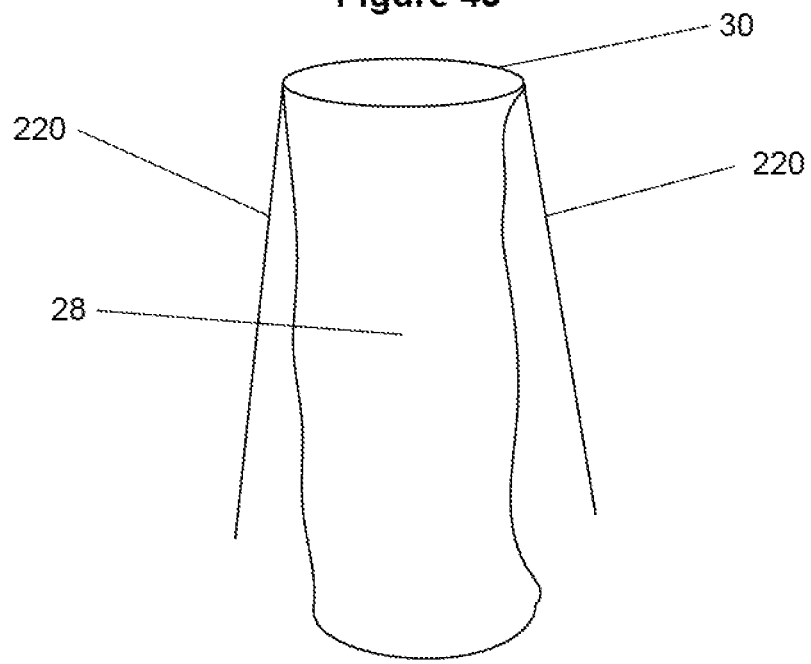
FIG. 43 illustrates an embodiment of the second implant.

As illustrated in FIG. 43, the second implant 28 can be attached to the seal ring 30 at the proximal end of the second implant 28. The seal ring 30 can be releasably attached to deployment rods 220.

Figure 44:
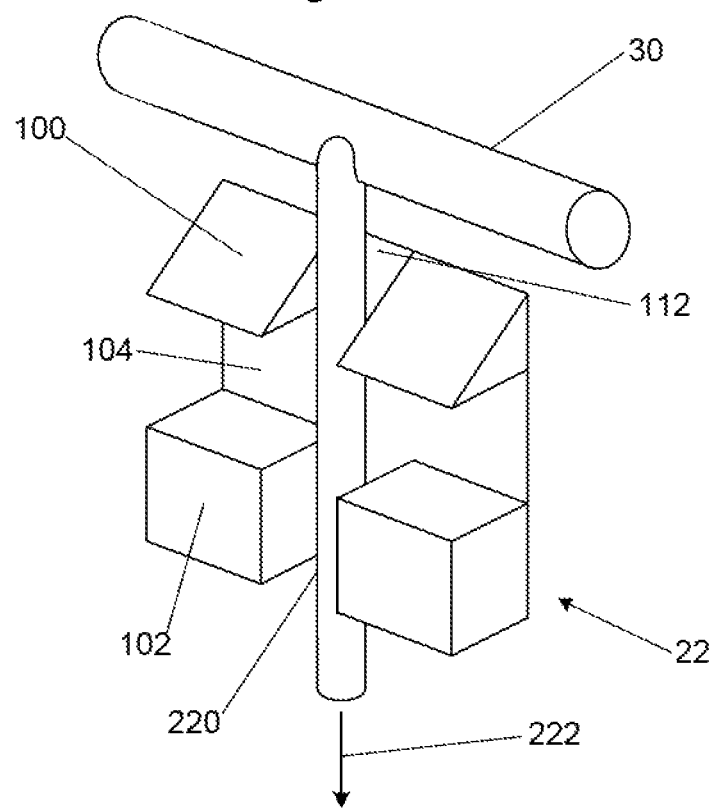
FIGS. 44 and 45 illustrate an embodiment of a method for attaching the seal to the attachment device.
Figure 45:
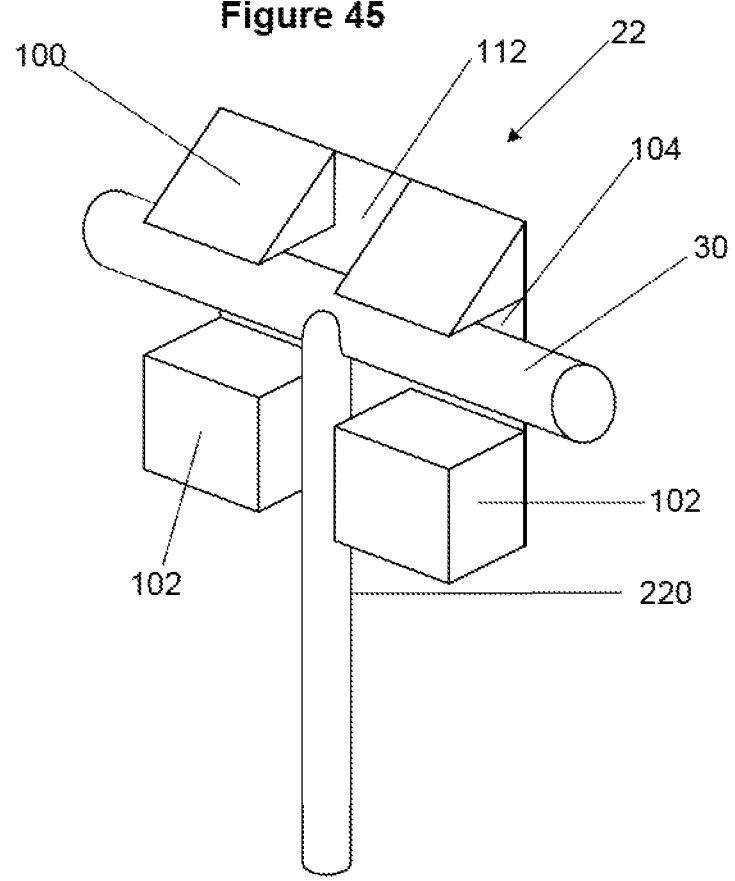

As illustrated in FIG. 44, the deployment rods 220 can be used to position the seal ring 30 proximal to the attachment device 22 and so that the deployment rods 220 align into the rod slots 112. (The second implant 28 is not shown in FIG. 44 for clarity). The deployment rods 220 can be pulled distally, as shown by arrow 222, thereby moving the seal ring 30 distally. As illustrated in FIG. 45, the seal ring 30 can then seat into the catch 104. The deployment rods 220 can be detached from the seal ring 30 and removed from the vascular site 170. The control line 172 can be removed from the vascular site 170 whenever removal is deemed appropriate during the implantation procedure.

FIG. 46 illustrates an embodiment of the intravascular implant 2 deployed at a vascular site 170. The vascular site 170 can have a severely tortuous region over which the implant 2 is placed. The flexibility of the connector 4 compensates for the contortion in the vascular site, enabling the arms 14 to intersect the wall of the vascular site 170 at a substantially perpendicular angle, and enabling the seal 20 to seat into the proximal neck 176 to open into the at a substantially parallel angle to the body of the second implant 28. Stress and fractures in the intravascular implant 2 and in the tissue at the vascular site 170 can be minimized due to the anchor 10 being mechanically insulated from the seal 20 by use of the connector 4. Additionally, stresses can be reduced because the tissue in the vascular site 170 adjacent to the anchor 10 does not need to seal, and the tissue in the vascular site 170 adjacent to the seal 20 does not need to anchor. Additional intravascular implants 2, as shown, can be deployed at the distal ends 224 of the second implant 2, for example in the iliac arteries, to additionally secure the second implant 2.

The arms 14 and/or the seal 20 can apply chronic stress to the adjacent tissue in the vascular site 170 causing a controlled migration of the arms 14 and/or seal 20 into the wall of the vascular site 170 to a specified depth predetermined by the tissue mainstays 33 and/or 148. The predetermined depth can be the length of the tissue mainstay 33 and/or 148, or a force exerted by the tissue mainstay 33 and/or 148. The controlled migration is then halted by either a distribution of force along the greater surface area between the tissue mainstay 33 and/or 148 and the wall of the vascular site 170 or the diminishing force on the same surface area once the radially central end (with respect to the anchor 10) of the tissue mainstay 33 and/or 148 has reached the wall of the vascular site 170, or a combination of both. Tissue can then ingrow around the tissue mainstay 33 and/or 148 providing a biologic seal or anchor so that the integrity of the seal or anchor is not purely mechanical.

It is apparent to one having ordinary skill in the art that various changes and modifications can be made to this disclosure, and equivalents employed, without departing from the spirit and scope of the invention. Elements shown with any embodiment are exemplary for the specific embodiment and can be used on other embodiments within this disclosure.

We claim:

1. A device for treating an aneurysm having a longitudinal axis, the device comprising:
   a bifurcated vascular graft comprising a main branch, a first leg, and a second leg, wherein the main branch is positionable across the aneurysm, and wherein the first leg and the second leg are positionable across the aneurysm;
   an inflatable seal;
   a first expandable anchor comprising first arms, wherein the first expandable anchor has a contracted configuration and an expanded configuration;
   a first leaf and a second leaf, wherein the first leaf and the second leaf are attached to the first expandable anchor, wherein the first leaf extends between two of the first arms, wherein the second leaf extends between two of the first arms,
   connectors attached to the first expandable anchor and to the inflatable seal, wherein the connectors have connector proximal ends and connector distal ends, wherein the connectors are between the first expandable anchor and the inflatable seal such that the connector proximal ends are attached to the first expandable anchor and such that the connector distal ends are attached to the inflatable seal; and
   flow ports between the first expandable anchor and the inflatable seal, wherein the flow ports are between adjacent connectors, and wherein the flow ports are between the connector proximal ends and the connector distal ends,
   wherein when the device is in a fully deployed configuration, the main branch extends across the aneurysm, the first leg extends across the aneurysm, the second leg extends across the aneurysm, and the first expandable anchor is in the expanded configuration in a blood vessel, wherein when the first expandable anchor is in the expanded configuration in the blood vessel, the expandable anchor contacts a first side of the blood vessel and a second side of the blood vessel opposite the first side of the blood vessel, and wherein when the first expandable anchor is in the expanded configuration in the blood vessel, the first leaf and the second leaf are pressed against the first side of the blood vessel,
   wherein when the device is in the fully deployed configuration, the first expandable anchor, the first leaf, the second leaf, the connectors, the flow ports, and the inflatable seal are proximal the aneurysm,
   wherein when the device is in the fully deployed configuration, the first expandable anchor, the first leaf, the second leaf, the connectors, and the flow ports are proximal the inflatable seal,
   wherein when the device is in the fully deployed configuration, the first expandable anchor is a proximal terminal end of the device,
   wherein the inflatable seal comprises a first seal portion and a second seal portion and a seal longitudinal axis, wherein the first seal portion is separated from the second seal portion by a first thin section and a second thin section, wherein an external surface of the first seal portion is a first distance from the seal longitudinal axis, wherein an external surface of the first thin portion is a second distance from the seal longitudinal axis, and wherein the first distance is greater than the second distance.

2. The device of claim 1, wherein the expandable anchor is configured to allow fluid to flow through the bifurcated vascular graft when the first expandable anchor is in the expanded configuration, and wherein the inflatable seal is configured to assist in holding the bifurcated vascular graft in place within the blood vessel.

3. The device of claim 1, further comprising a third leaf, wherein the third leaf is attached to the first expandable anchor, and wherein the third leaf extends between two of the first arms.

4. The device of claim 3, further comprising a fourth leaf, wherein the fourth leaf is attached to the first expandable anchor, and wherein the fourth leaf extends between two of the first arms.

5. The device of claim 4, wherein when the device is in the fully deployed configuration, the third leaf and the fourth leaf are opposite the first leaf and the second leaf.

6. The device of claim 5, wherein a distal end of the inflatable seal is attached to or integrated with the main branch, wherein when the device is in the fully deployed configuration, a proximal end of the main branch is proximal the aneurysm.

7. The device of claim 6, wherein when the device is in the fully deployed configuration, the first expandable anchor is proximal the renal arteries and the inflatable seal is distal the renal arteries.

8. The device of claim 7, wherein when the first expandable anchor is in the contracted configuration, the first arms are biased to radially expand.

9. The device of claim 7, wherein pairs of connectors form x-beams, and wherein the flow ports extend around a circumference of the device longitudinal axis.

10. The device of claim 7, further comprising a second expandable anchor and a third expandable anchor, wherein the second expandable anchor is attached to the first leg and is expandable distal a distal terminal end of the first leg, wherein the third expandable anchor is attached to the second leg and is expandable distal a distal terminal end of the second leg, wherein when the second expandable anchor is in a contracted configuration, the second expandable anchor is biased to radially expand, and wherein when the third expandable anchor is in a contracted configuration, the third expandable anchor is biased to radially expand.

11. A device for treating an aneurysm having a longitudinal axis, the device comprising:
a bifurcated vascular graft comprising a main branch, a first leg, and a second leg, wherein the main branch is positionable across the aneurysm, wherein the first leg and the second leg are positionable across the aneurysm;
an inflatable seal integrated with a proximal end of the main branch;
first expandable anchor arms proximal the inflatable seal;
second expandable anchor arms proximal the inflatable seal, wherein the second expandable anchor arms are between the first expandable anchor arms and the inflatable seal;
a first leaf, a second leaf, a third leaf, and fourth leaf proximal the inflatable seal, wherein the first expandable anchor arms, the second expandable anchor arms, the first leaf, the second leaf, the third leaf, and the fourth leaf are expandable against a wall of a blood vessel, wherein the first leaf extends between two of the first expandable anchor arms, wherein the second leaf extends between two of the first expandable anchor arms, wherein the third leaf extends between two of the first expandable anchor arms, wherein the fourth leaf extends between two of the first expandable anchor arms, and wherein the first leaf and the second leaf are opposite the third leaf and the fourth leaf; and
connectors proximal the inflatable seal, wherein the first expandable anchor arms and the second expandable anchor arms are connected to the inflatable seal via the connectors,
wherein when the device is in a fully deployed configuration, the main branch extends across the aneurysm, the first leg extends across the aneurysm, the third leg extends across the aneurysm, the first expandable anchor arms are in an expanded configuration in the blood vessel, and the second expandable anchor arms are in an expanded configuration the blood vessel,
wherein when the device is in the fully deployed configuration, the first expandable anchor arms, the second expandable anchor arms, the first leaf, the second leaf, the third leaf, the fourth leaf, the connectors, and the inflatable seal are proximal the aneurysm,
wherein when the device is in the fully deployed configuration, the first expandable anchor arms are inverted relative to the second expandable anchor arms,
wherein when the device is in the fully deployed configuration, the first expandable anchor arms are a proximal terminal end of the device, and
wherein the inflatable seal comprises a first seal portion, a second seal portion, and a seal longitudinal axis, wherein the first seal portion is separated from the second seal portion by a first thin section, and wherein the first and second seal portions are inflatable.

12. The device of claim 11, wherein the first expandable anchor arms and the second expandable anchor arms are configured to allow fluid to flow through the bifurcated vascular graft when the first expandable anchor arms are in the expanded configuration and when the second expandable anchor arms are in the expanded configuration, and wherein the inflatable seal is configured to assist in holding the bifurcated vascular graft in place within the blood vessel.

13. The device of claim 11, wherein the bifurcated vascular graft is placeable across an abdominal aortic aneurysm.

14. The device of claim 11, wherein when the device is in the fully deployed configuration, the first anchor arms are proximal the renal arteries and the inflatable seal is distal the renal arteries.

15. The device of claim 11, wherein when the device is in the fully deployed configuration, the first and second expandable anchor arms are angled relative to a device longitudinal axis, wherein when the first expandable anchor arms are in a contracted configuration, the first expandable anchor arms are biased to radially expand, and wherein when the second expandable anchor arms are in a contracted configuration, the second expandable anchor arms are biased to radially expand.

16. A device for treating an aneurysm having a longitudinal axis, the device comprising:
a bifurcated vascular graft comprising a main branch, a first leg, and a second leg;
a first expandable anchor, a second expandable anchor, and a third expandable anchor;
a first inflatable ring attached to the main branch, a second inflatable ring attached to the first leg, and a third inflatable ring attached to the second leg; and
a first connector, a second connector, and a third connector, wherein the first expandable anchor is connected to the first inflatable ring via the first connector, wherein the second expandable anchor is connected to the second inflatable ring via the second connector, and wherein the third expandable anchor is connected to the third inflatable ring via the third connector,
wherein the first expandable anchor is expandable proximal a proximal terminal end of the main branch, wherein the second expandable anchor is expandable distal a distal terminal end of the first leg, and wherein the third expandable anchor is expandable distal a distal terminal end of the second leg,
wherein when the device is in a fully deployed configuration, the main branch extends across the aneurysm, the first leg extends across the aneurysm, and the third leg extends across the aneurysm,
wherein when the device is in the fully deployed configuration, the first expandable anchor is in an expanded configuration proximal the proximal terminal end of the main branch in a first blood vessel, the second expandable anchor is in an expanded configuration distal the distal terminal end of the first leg in a second blood vessel, and the third expandable anchor is in an expanded configuration distal the distal terminal end of the second leg in a third blood vessel, wherein when the device is in the fully deployed configuration, the first expandable anchor is proximal the aneurysm, the second expandable anchor is distal the aneurysm, and the third expandable anchor is distal the aneurysm, wherein when the device is in the fully deployed configuration, the first connector extends proximally away from the first inflatable ring such that the first connector and the first expandable anchor are proximal the first inflatable ring, wherein when the device is in the fully deployed configuration, the second connector extends distally away from the second inflatable ring such that the second connector and the second expandable anchor are distal the second inflatable ring, and wherein when the device is in the fully deployed configuration, the third connector extends distally away from the third inflatable ring such that the third connector and the third expandable anchor are distal the third inflatable ring.

17. The device of claim 16, further comprising flow ports between the first inflatable ring and the first expandable anchor, wherein the flow ports face away from a device longitudinal axis, wherein when the first expandable anchor is in a contracted configuration, the first expandable anchor is biased to radially expand, wherein when the second expandable anchor is in a contracted configuration, the second expandable anchor is biased to radially expand, wherein when the third expandable anchor is in a contracted configuration, the third expandable anchor is biased to radially expand, wherein the first expandable anchor is contractible proximal the proximal terminal end of the main branch, wherein the second expandable anchor is contractible distal the distal terminal end of the first leg, and wherein the third expandable anchor is contractible distal the distal terminal end of the second leg.

* * * * *